United States Patent
Romano

(10) Patent No.: US 10,758,710 B2
(45) Date of Patent: Sep. 1, 2020

(54) ACCESS AND SUPPORT CATHETER

(71) Applicant: PIPE Therapeutics LLC, Gladwyne, PA (US)

(72) Inventor: John-Paul Romano, Chalfont, PA (US)

(73) Assignee: PIPE Therapeutics LLC, Gladwyne, PA (US)

( * ) Notice: Subject to any disclaimer, the term of this patent is extended or adjusted under 35 U.S.C. 154(b) by 0 days.

(21) Appl. No.: 16/273,119

(22) Filed: Feb. 11, 2019

(65) Prior Publication Data

US 2019/0247620 A1 Aug. 15, 2019

Related U.S. Application Data

(60) Provisional application No. 62/651,049, filed on Mar. 30, 2018, provisional application No. 62/629,069, filed on Feb. 11, 2018.

(51) Int. Cl.
*A61M 25/01* (2006.01)
*A61M 25/10* (2013.01)
*A61M 25/09* (2006.01)

(52) U.S. Cl.
CPC ........ *A61M 25/0152* (2013.01); *A61M 25/09* (2013.01); *A61M 25/0113* (2013.01); *A61M 25/10* (2013.01); *A61M 2025/09125* (2013.01)

(58) Field of Classification Search
CPC .............. A61M 25/0152; A61M 25/09; A61M 25/0013; A61M 25/0015; A61M 25/0054; A61M 25/10; A61M 2025/09125
See application file for complete search history.

(56) References Cited

U.S. PATENT DOCUMENTS

| | | | |
|---|---|---|---|
| 670,748 | A | 3/1901 | Weddeler |
| 2,515,365 | A | 7/1950 | Zublin |
| 2,515,366 | A | 7/1950 | Zublin |
| 4,362,520 | A | 12/1982 | Perry |
| 5,178,129 | A | 1/1993 | Chikama et al. |
| 5,325,845 | A | 7/1994 | Adair |
| 5,437,288 | A | 8/1995 | Schwartz et al. |
| 5,573,520 | A | 11/1996 | Schwartz et al. |
| 5,741,429 | A | 4/1998 | Donadio, III et al. |
| 6,758,854 | B1 | 7/2004 | Butler et al. |
| 8,376,865 | B2 | 2/2013 | Forster et al. |
| 9,782,566 | B1 | 10/2017 | Paprocki et al. |
| 2003/0069522 | A1 | 4/2003 | Jacobsen et al. |
| 2005/0080400 | A1* | 4/2005 | Corcoran .......... A61M 25/0054 604/523 |
| 2008/0108904 | A1 | 5/2008 | Heil |
| 2010/0331776 | A1 | 12/2010 | Salahieh et al. |
| 2011/0313417 | A1 | 12/2011 | De La Rama et al. |

(Continued)

FOREIGN PATENT DOCUMENTS

WO WO2017/117092 A1 7/2017

OTHER PUBLICATIONS

Romano; U.S. Appl. No. 16/273,126 entitled "Access and support catheter methods of Use" filed Feb. 11, 2019.

(Continued)

*Primary Examiner* — Kevin C Sirmons
*Assistant Examiner* — Tezita Z Watts
(74) *Attorney, Agent, or Firm* — Shay Glenn LLP

(57) ABSTRACT

Described herein are bend-limited catheters (e.g., apparatuses, including devices and systems) and methods of using them.

27 Claims, 30 Drawing Sheets

Spiral Design, variable density down length of tube

(56) References Cited

U.S. PATENT DOCUMENTS

| | | |
|---|---|---|
| 2012/0232494 A1 | 9/2012 | Tanaka et al. |
| 2013/0085479 A1 | 4/2013 | de la Rama et al. |
| 2016/0345947 A1 | 12/2016 | Salahieh et al. |
| 2017/0252536 A1 | 9/2017 | Yang et al. |
| 2018/0015257 A1 | 1/2018 | Krolik et al. |
| 2018/0326178 A1* | 11/2018 | Moquin ................ A61L 29/041 |
| 2019/0247621 A1 | 8/2019 | Romano |
| 2019/0247622 A1 | 8/2019 | Romano |

OTHER PUBLICATIONS

Romano; U.S. Appl. No. 16/273,135 entitled "Bend-limited catheters" filed Feb. 11, 2019.

* cited by examiner

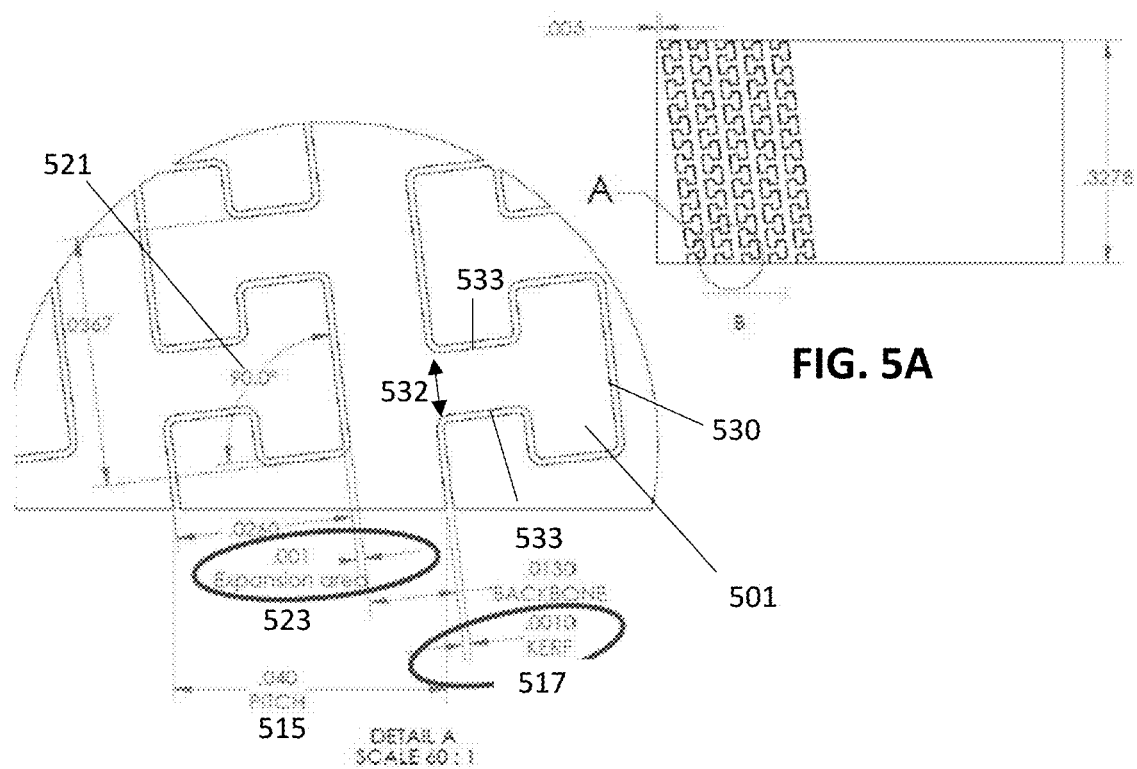
FIG. 5A
FIG. 5B
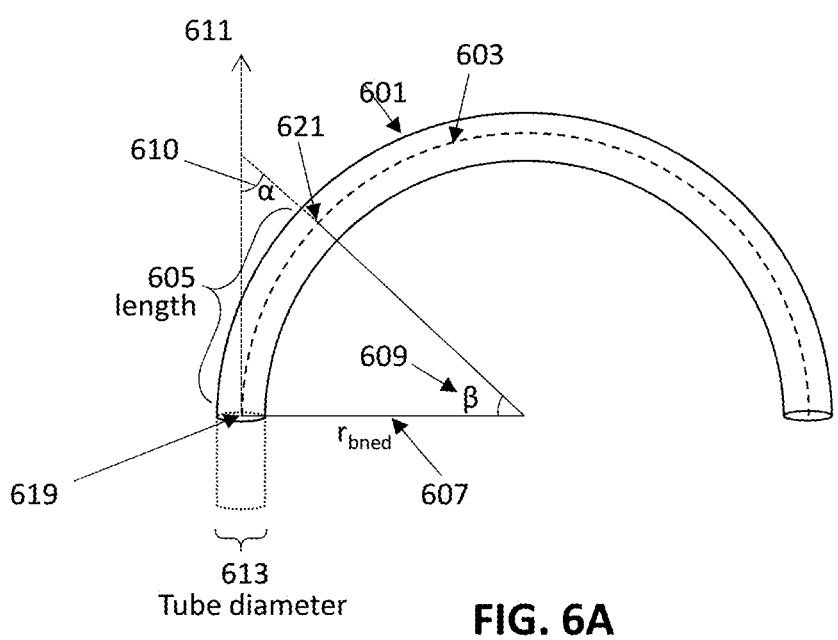
FIG. 6A

| Variable | Input | Output | Range |
|---|---|---|---|
| Material | Stiffer | Less likely to ovalize, kink or allow Teeth to disengage. More likely to spring towards an set orientation. | Tungsten, Steel, Other metals, Nitinol, Rigid Polymers |
| Expansion area per unit length (tube) | More | Decreases minimum bend radius. Increases amount of bending. | 1% - 85% For example: (0.001" per 0.1" - 0.085" per 0.1") |
| Expansion area per unit length (tube) | Less | Increases minimum bend radius. Decreases amount of bending. | 1% - 85% For example: (0.001" per 0.1" - 0.085" per 0.1") |
| Tube Outer Diameter | Smaller | Smaller relative bend radius possible | 0.011" - 1.501" |
| Tube Inner Diameter | Larger | Smaller relative bend radius possible | 0.010" - 1.5" |
| Tooth Angle | Larger | Greater expansion area | 0 - 85 degrees |
| Pitch | Larger | Less interlocking sections per unit length. Less expansion per unit length. | 0.005" - 0.3" |
| Teeth per Revolution | More | Allows more torsional displacement, less torsional stiffness. Smoother inner and outer surfaces | 3-50 |
| Backbone width | Larger | Greater stiffness. Less likely to ovalize, kink, or allow Teeth to disengage. If increases Pitch, less expansion per unit length. | 0.002" - 0.060" |
| Pattern Angle | | Largely driven by Tooth height, Backbone width, and Kerf. | 1 - 40 degrees |
| Tooth Shape | Varied | Keystone, "T", Circular, Skewed or Direction-Biased, "L", Combinations | |
| Number of Leads | Greater | Requires greater Pattern Angle. | 1-3 |

FIG. 7A

| Variable | Input | Output |
|---|---|---|
| Outer lamination protruding in-between cuts in ES | More | Reduces range of motion. Increases cushioning in compression |
| Inner lamination protruding in-between cuts in ES | More | Reduces range of motion. Increases cushioning in compression |
| Outer lamination elasticity | More | Increased catheter flexibility. Less rigidity. |
| Inner lamination elasticity | More | Increased catheter flexibility. Less rigidity. |
| Intentionally uneven distribution of Outer lamination protrusion in-between ES cuts | Directional, zig-zag, helical, shaped, etc. patterns. | Directional, zig-zag, helical, shaped etc. pattern bending bias, bending limits. |
| Intentionally uneven distribution of Inner lamination protrusion in-between ES cuts | Directional, zig-zag, helical, shaped, etc. patterns. | Directional, zig-zag, helical, shaped etc. pattern bending bias, bending limits. |
| Varying ES cut geometry around radius (kerf, tooth angle, tooth shape) | Increasing expansion area at radial positions. | More expansion possible in those zones, greater bending there. Directional, zig-zag, helical, shaped etc. pattern bending bias, bending limits. |

FIG. 7B

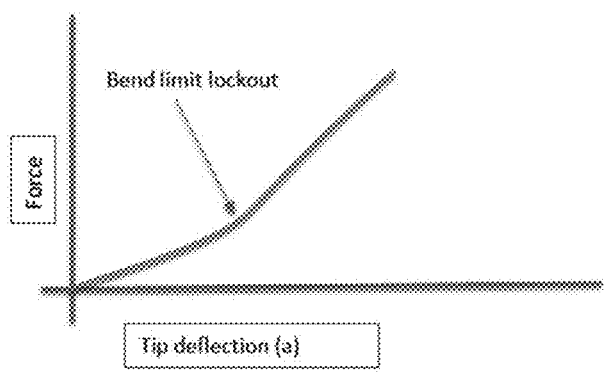

FIG. 8A

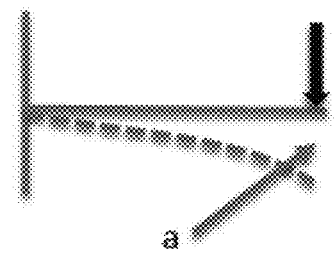

FIG. 8B

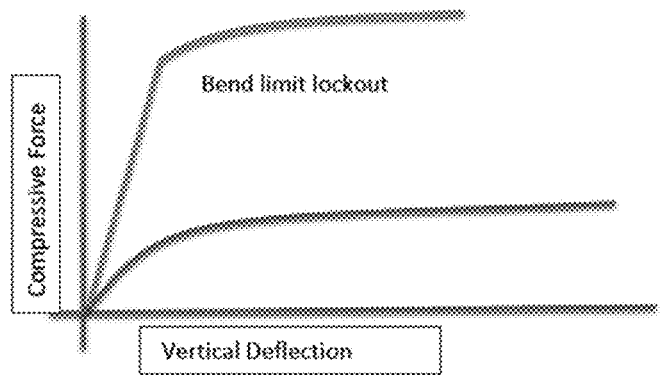
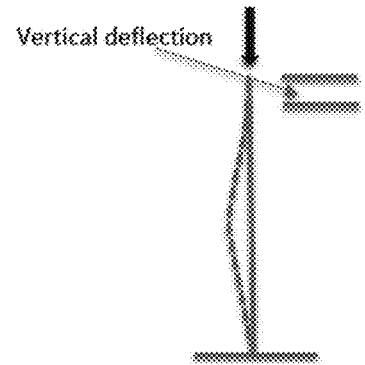
FIG. 9A
FIG. 9B
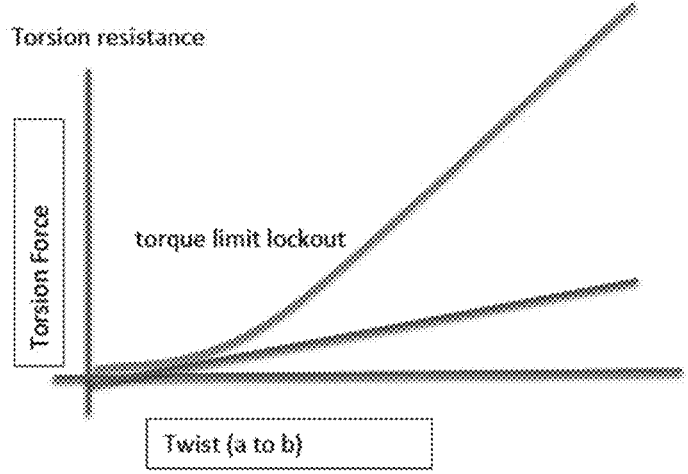
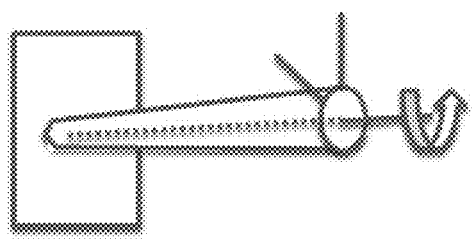
FIG. 10A
FIG. 10B

FIG. 16 For catheter straightening, puller closer to central axis
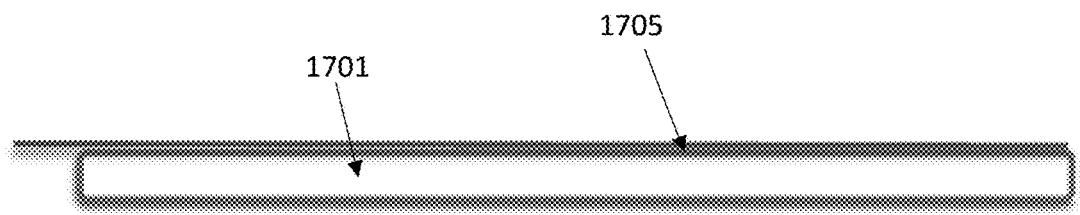
FIG. 17A
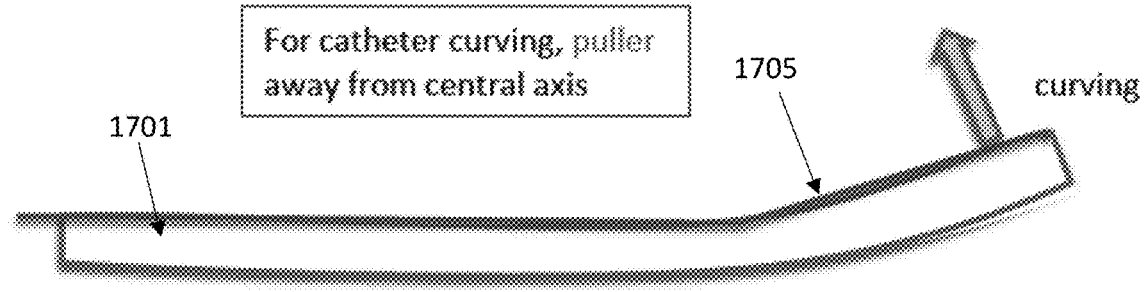
FIG. 17B For catheter curving, puller away from central axis
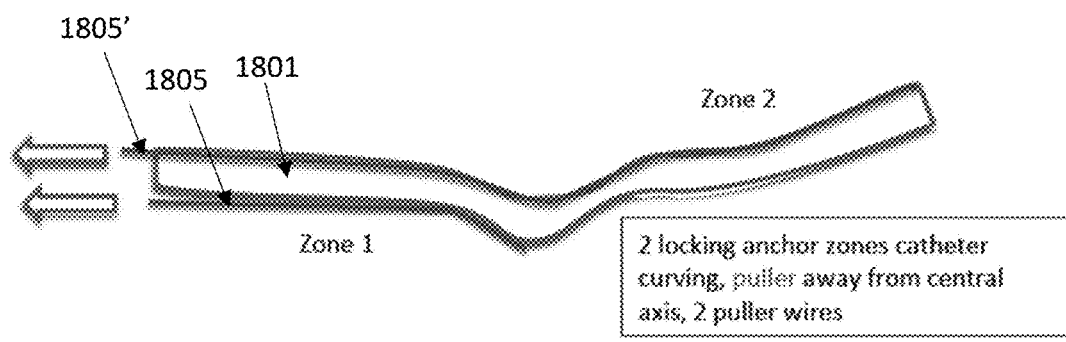
FIG. 18 2 locking anchor zones catheter curving, puller away from central axis, 2 puller wires

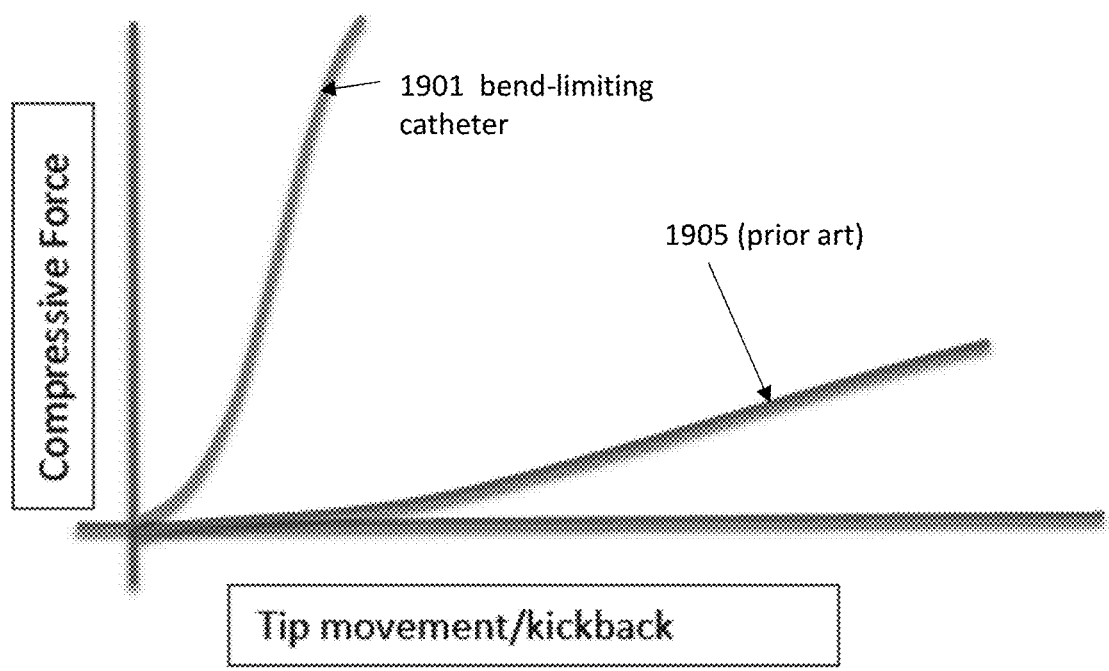
FIG. 19
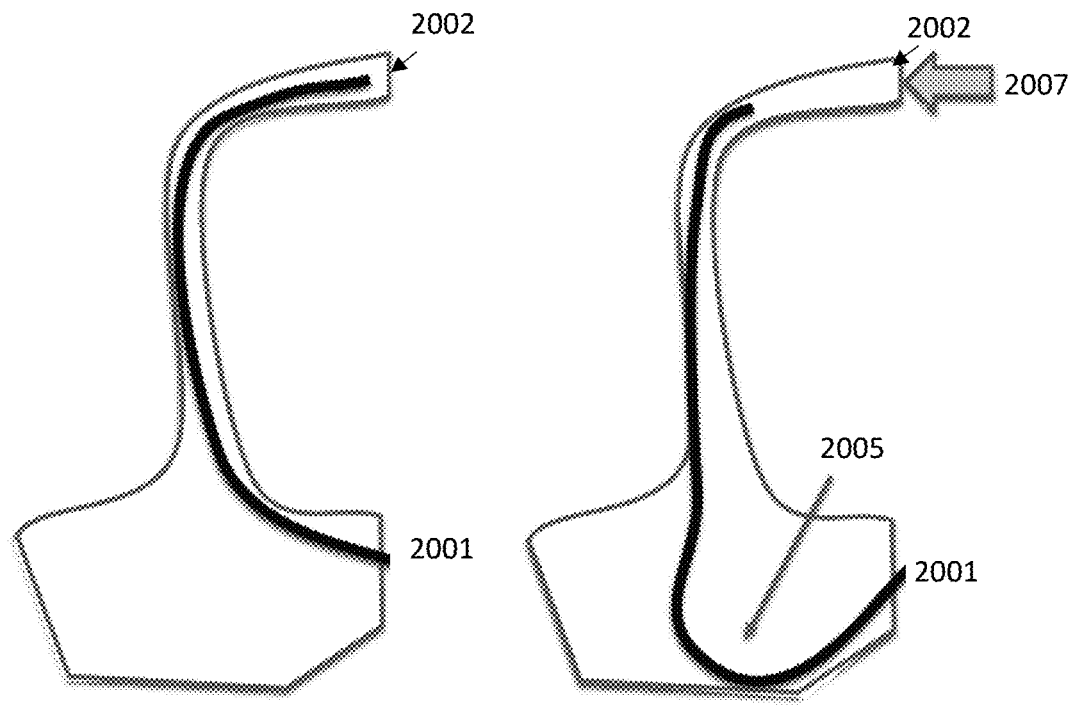
FIG. 20A    FIG. 20B telescoping tubing lock.

Directional Friction catheter feature.

Non Spiral Design, variable density down length of tube

Spiral Design, variable density down length of tube

ACCESS AND SUPPORT CATHETER

CROSS REFERENCE TO RELATED APPLICATIONS

This patent application claims priority to U.S. Provisional Patent Application No. 62/629,069, titled "SUPPORTIVE CATHETER," filed on Feb. 11, 2018 and U.S. Provisional Patent Application No. 62/651,049, titled "SUPPORTIVE CATHETER," filed on Mar. 30, 2018, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Catheter devices and methods for using them for insertion into the body during medical procedures that are loose and flexible up to a predetermined locking angle that avoid kinking, prolapse and kickback. More particularly, described herein are flexible tubular catheters, including guide catheters and balloon catheters, guide catheters, drug infusion catheters, and the like, as well as methods of using and making them.

BACKGROUND

Catheters are tubular devices that may be used in the medical field for numerous applications. It is generally desirable to obtain a maximum torsional rigidity while retaining a satisfactory longitudinal flexibility and stiffness without kinking. These features may allow the orientation of the catheter to be manipulated so that the catheter can be guided through small body vessels and cavities. These features may also prevent any kinking, and may provide the catheter with enough "push" or stiffness so as to prevent the catheter from wrinkling or folding back on itself during this process. The specific nature of these characteristics may vary depending on the specific application for which the catheter is being used. It may also be beneficial to provide a relatively small outside diameter and a lumen or an inside diameter as large as possible.

Catheters (with our without guide wires) may be used both as a diagnostic tool and in the treatment of diseases. One such diagnostic procedure is cardiac catheterization which is a widely performed procedure, being used for assessment of coronary artery disease. Other uses are neurologic uses, radiologic uses, electrophysiologic uses, peripheral vascular uses, etc. One example of a treatment use is the use of balloon catheters in dilation procedures to treat coronary disease. Dilation procedures rely upon the use of a catheter for injection of contrast and delivery of guidewires and dilation catheters to the coronary artery or other arteries. An example of the use of guide wires is for Percutaneous Transluminal Coronary Angioplasty (PTCA) balloons and for guiding diagnostic catheters through the arteries and to body organs.

The catheters and guide wires used in these and other procedures must have excellent torque characteristics, and must have the requisite flexibility. In addition, it is important that catheters and guidewires provide sufficient longitudinal support for "pushing" of items through the arteries and other vessels such as when feeding the balloon portion of an angioplasty catheter through the arteries. Unless there is sufficient stiffness, the catheter or guidewire will wrinkle or fold back on itself. Catheters should ideally have sufficient torque such that they do not buckle when being manipulated. Flexibility may be important so that the catheter can be manipulated into the varying arterial branches encountered by the catheter.

Prior art catheters are typically made of flexible materials which are reinforced such that the resulting composite catheter approximates the desired characteristics. In alternative approaches, guide wires are used in conjunction with catheters to assist in manipulating and moving the catheters through the arterial system in the body. Described herein are catheters are highly flexible, while maintaining stability, preventing kickback and resisting prolapse and kinking.

SUMMARY OF THE DISCLOSURE

Described herein are bend-limited catheter apparatuses, e.g., devices and systems, and methods of using them to perform a medical procedure. In general, the apparatuses described herein may include an elongate tubular body that includes one or more cut-out kerfs forming a pattern of interlocking teeth that are arranged in rings (and/or one or more spiral patterns) around the perimeter of the elongate tubular body. The pattern of interlocking teeth is configured, as described in greater detail herein, to provide the catheter with a high degree of flexibility in bending, while permitting the device to lock at a locking diameter (or locking radius) when the relevant portion of the catheter bends to a minimum locking angle, or minimum locking angle per unit length corresponding to the locking diameter, beyond which no further bending is permitted. The cut-out kerf(s) may be sealed, e.g., by a compressible material, such as a polymer, so that the catheter walls are fluid-tight, which may be referred to herein as a jacket or seal.

Generally, the bend-limited catheters described herein may be configured to be highly flexibility until bent to the locking bend angle. In some variations the portion(s) of the catheter including the pattern of interlocking teeth arranged radially around the perimeter and extending down the length of the tubular body may be loose, or floppy, when initially bending from the straight, unbent configuration until bent to the locking bend angle, preventing further bending. In addition, the bend-limited catheters described herein may be thin (e.g., have a small wall thickness) and the pattern of interlocking teeth may be configured so that the catheters are highly smooth, while remaining lockable and highly flexible.

These features (e.g., smoothness, lockability and flexibility) may be achieved in a thin-walled, e.g., metal or rigid polymeric, tube by forming the pattern of interlocking teeth in which each tooth has dimensions, including tooth angle, tooth height, tooth spacing (e.g., pitch, such as pitch/catheter diameter), and tooth number that increase smoothness, permitting a high level of flexibility without reducing the strength of the catheter under bending (including compressive) loads. The catheters described herein typically have an outer and inner smoothness that permits the use of inserted devices without risking snagging or cutting. Smoothness of these bend-limited catheters may be, at least in part, a function of the low pitch angle (and small backbone region), as well as the number of teeth; a larger number of smaller, and/or shorter teeth may provide a smoother surface. Unfortunately, smaller number and/or heights for the interlocking teeth typically results in lower flexibility and may decrease the strength of the catheter. In general, the larger the pitch, or the spacing between adjacent rows/spirals of interlocking teeth along the length of the catheter, which may include the height of the teeth in the length of the catheter and the backbone spacing between adjacent rows/spirals, may generally increase flexibility while reducing smoothness (particularly where the contribution of backbone spacing to the pitch is small, e.g., less than 50%) and may permit a larger locking diameter. Thus, described herein are ranges of values that may balance these often conflicting properties to provide bend-limited catheters that may be used for a variety of medical uses, including neurovascular and cardiovascular uses.

Any of the bend-limited catheters described herein, which may be referred to herein as bend-limited catheter apparatuses or bend-limited catheter devices, may include a tubular body having one or more cut-out kerfs forming a pattern of interlocking and alternating teeth extending around the tubular body, wherein each tooth of the interlocking and alternating teeth comprises a head region that is wider than a base region, arranged so that the head regions alternate with base regions radially around the tubular body, so that the first region bends in a direction out of a long axis of a catheter device up to a locking radius, beyond which the tubular body does not allow further bending in the direction. The pattern of interlocking and alternating teeth may extend along the entire length of the tubular body, or just along one or more regions (e.g., a first region, a second region, a third region, etc.) of the length of the tubular body. In variation in which multiple regions along the length of the tubular body include a pattern of interlocking and alternating teeth, the same pattern may be used or different patterns may be used, which may provide different regions having different smoothnesses, flexibilities, and/or locking bend angle(s). When the bend-limited catheter includes multiple regions along the length of the tubular body are used, these regions may be immediately adjacent to each other or they may be separated from each other by a transition region and/or by a region that does not include interlocking and alternating teeth. A transition region may have a pattern of interlocking and alternating teeth that transitions between the pattern of interlocking and alternating teeth in the proximally-located region of the catheter and the pattern of interlocking and alternating teeth in the distally-located region of the catheter. The transition may be gradual or abrupt.

Any of the catheters described herein may include a sleeve, seal, skin, cover, sheath, or the like that may comprise a sealing material, which may be a compressible material. extending across the cut-out kerf. For example, the sealing material may be laminated to the rigid tubular body (e.g., to an inner surface, an outer surface, or both). In some variations the sealing material is positioned between the inner and outer surfaces of the tubular body, including within the cut-out kerf. Any appropriate sealing material may be used. The sealing material may be a polymeric material. In particular, the sealing material may be a thin layer, coating, film, etc. (e.g., about 0.01 inches or less thick, about 0.009 inches or less, about 0.008 inches or less, about 0.007 inches or less, about 0.006 inches or less, about 0.005 inches or less, about 0.004 inches or less, about 0.003 inches or less, about 0.002 inches or less, about 0.001 inches or less, etc.). The sealing material may be a material having a relatively high (e.g., Shore A) durometer, such as materials having a shore A durometer of about 60 or greater, about 65 or greater, about 70 or greater, about 75 or greater, about 80 or greater, etc.

The interlocking and alternating teeth of the bend-limited catheter devices described herein may be any appropriate shape or variety of shapes, such as keystone shapes, a mushroom shapes, and a T-shapes. In particular, the alternating teeth may be keystone shapes. A keystone shape generally has a larger top region, which may be flat or flattened, with sharp or rounded edges and sides that extend at an angle relative to the top (one example of a tooth angle) to a base, so that the base diameter is narrower than the top. As illustrated herein the base region of a tooth forms the top region of the alternate next tooth. Thus, the pattern of interlocking and alternating teeth may be a pattern of interlocking and alternating keystone-shaped teeth.

For example, a bend-limited catheter device having a length extending in a long axis, may include: a tubular body having a first region of one or more cut-out kerfs forming a pattern of interlocking and alternating keystone-shaped teeth extending around the tubular body, wherein each tooth of the interlocking and alternating teeth comprises a head region that is wider than a base region, arranged so that the head regions alternate with base regions radially around the tubular body, so that the first region bends freely in a direction out of a long axis of the catheter device with a lateral stiffness that is less than 100 grams up to a locking radius, beyond which the tubular body does not allow further bending in the direction; and a sealing material extending across the cut-out kerf.

In any of the catheters described herein, the expansion between adjacent teeth of the interlocking and alternating teeth may be greater than a diameter of the one or more cut-out kerfs. Expansion between adjacent teeth may occur because the side of the teeth, e.g., in a keystone-shaped tooth, the angled, lateral sides of the keystone shape extending between the top and base, slide relative to each other in approximately the long axis of the catheter (e.g., distal to proximal). The length of the lateral sides along which this sliding occurs may be maximized in some variations (e.g., may be X % or greater than the height of the tooth, where X is 20, 25, 30, 25, 40, 50, etc.). For example, the pattern of interlocking and alternating teeth may be configured to expand from a compressed elongate length by between about 0.005 inches and 0.085 inches per every 0.1 inch of the length of the pattern. In some variations (or regions) having a kerf diameter of about 0.001 inches, the pattern of interlocking and alternating teeth may be configured to expand by about 0.002" for each mating set of teeth; in some variation (or regions), the pattern of interlocking and alternating teeth may be configured to expand by about 0.005" for each mating set of teeth (e.g., between 0.002 inches and 0.010 inches).

The pattern of interlocking and alternating teeth may include any appropriate number of teeth per revolution around the diameter of the tubular body that can be fit with the pitch and dimensions described herein. As mentioned above, it may be beneficial to balance the number of smaller teeth (increasing flexibility at the possible expense of minimum bend diameter) with larger teeth (decreasing flexibility but increasing minimum bend diameter). For example, the tubular body may comprise a minimum of 18 teeth per revolution around the diameter of the tubular body (or between 6-70 teeth per revolution, between 12-65 teeth per revolution, between 15-62 teeth per revolution, between 18-60 teeth per revolution, between 20-60 teeth per revolution, 15 or more teeth/revolution, 18 or more teeth/revolution, 20 or more teeth/revolution, 22 or more teeth/revolution, etc.

In any of the catheters described herein, the ratio of the pitch of the teeth to the tubular body diameter may be between 0.09 and 0.90 (e.g., between 0.1 and 0.9, between 0.12 and 0.85, between 0.10 and 0.50, etc.). The pitch may refer to the distance between adjacent rows of interlocking and alternating teeth along the long axis of the tubular body, including the height of the teeth; for example, the pitch may be the height of the teeth (the distance between the head region and the base region) and the backbone distance before the start of the next loop of interlocking teeth in the long axis. The diameter of the tubular body may be measured transverse to the portion of the tubular body (e.g., transverse to the long axis of the tubular body) at or around the location of the interlocking teeth defining the pitch measurement. As mentioned above, in some variations the pitch may include both the height of the teeth and the backbone portion separating long-axis adjacent teeth; the portion of the backbone in the pitch may be, e.g., 60% or less, 55% or less, 50% or less, 45% or less, 40% or less, 35% or less, 30% or less, 25% or less, 20% or less, etc. and may have a minimum of 2%, 5%, 7%, 10%, etc. (e.g., between about 2% and 50%, between about 5%-55%, 7.5%-50%, etc.).

In general, the pattern of interlocking and alternating teeth may be configured so that the tooth angle is within a range that permits the expansion area of the catheter device to be within predefined limits, while permitting increased flexibility, smoothness and a locking angle within a defined range. For example, the teeth of the pattern of interlocking and alternating teeth may form a tooth angle between a line extending through a width of the head region (or in keystone-shaped teeth the flat or flattened top) and a line extending from the head region and the base region (e.g., the sides of the keystone-shaped teeth) of between about 40 degrees and about 89 degrees; in some variations between about 40 degrees and about 65 degrees (e.g., between about 40 and about 60 degrees, etc., between about 45 and about 65 degrees, between about 45-63 degrees, etc.), in some variations between about 66 and about 87 degrees (e.g., between about 68 and about 84 degrees, between about 66 and about 82 degrees, etc.).

The tubular body may be formed of generally inflexible, e.g., rigid, material. For example, in some variations, the tubular body may be a rigid material such as one or more of: steel, tungsten, and Nitinol. The tubular body may therefore be cut (e.g., laser cut) to form the one or more cut-out kerfs forming a pattern of interlocking and alternating teeth. The cut-out kerf may have any appropriate diameter, including constant or near-constant (within +/−2%, 5%, 7.5%, etc.) diameter along its length(s), or it may vary. In some variations, the kerf has a diameter of between about 0.005 inches and 0.0005 inches (e.g., about 0.001 inches, about 0.002 inches, about 0.0009 inches, etc.).

The pattern of interlocking and alternating teeth may generally have a ratio of the bend radius to a diameter of the tubular body of between about 1 and 25 (e.g., between about 1.5 to 22.5, etc.). The ration of the bend radius of a region of the tubular body including the pattern of interlocking and alternating teeth to the diameter of the kerf forming the pattern may be between about 100 and 2100 (e.g., between about 120 and 2000, 2100 or less, 2050 or less, 2000 or less, 1950 or less, etc.).

Any of the catheter devices described herein may include one or more balloons, e.g., inflatable balloon elements, along the length of the device. For example, any of these catheter devices may include an inflatable balloon on the catheter, including, but not limited to, at or near a distal end of the catheter.

In general, the bend-limited catheter devices described herein may be configured to have a locking radius, as mentioned above, that is between about 0.1 cm and about 40 cm, e.g., between about 0.2 cm and about 35 cm, between about 0.2 cm and 30 cm, between about 0.3 cm and about 28 cm, between about 0.4 cm and about 27 cm, between about 0.5 cm and about 26 cm, etc.

For example, a bend-limited catheter device having a length extending in a long axis, may include: a tubular body having a first region of one or more cut-out kerfs forming a pattern of interlocking and alternating keystone-shaped teeth extending around the tubular body, wherein each tooth of the interlocking and alternating keystone-shaped teeth comprises a head region that is wider than a base region, arranged so that the head regions alternate with base regions radially around the tubular body, so that the first region bends in a direction out of a long axis of the catheter device up to a locking radius of between 0.2 cm and 30 cm, beyond which the tubular body does not allow further bending in the direction, wherein each tooth of the interlocking and alternating teeth form a tooth angle between a line extending through a width of the head region and a line extending from the head region and the base region that is between 40 and 84 degrees, further wherein the pitch to tubular body diameter ratio of the first region is between 0.09 and 0.90, wherein pitch is a distance between adjacent rows of interlocking and alternating teeth along the long axis of the tubular body; and a sealing material extending across the cut-out kerf.

Any of the catheters, and systems including them, described herein may include a plurality of different regions that may be configured to have different maximum bend angles (e.g., locking angles), flexibility and/or smoothness. In particular, it may be particularly helpful to provide catheters having different regions of cut-out kerfs forming one or more patterns of interlocking and alternating teeth extending around the tubular body that have different flexibilities and different bend angles in a distal region as compared to a proximal region. For example, a bend-limited catheter as described herein may include one or more cut-out kerfs forming a pattern of interlocking and alternating teeth extending around the tubular body that is/are configured so that a distal region of the catheter has a higher tooth angle and lower ratio of pitch to tube diameter as compared to a more proximal region of the catheter (which therefore has a lower tooth angle and a high ratio of pitch to tube diameter). This configuration may have a distal region having a smaller bend diameter/bend radius as compared to a distal region having a larger bend diameter/bend radius (e.g., locking radius). The second region may correspond to a region within the anatomy of a patient in which the catheter is configured to be inserted; the minimum bend angle or locking angle may correspond to the aortic region of the anatomy, where it may be desirable to prevent excessive bending or bucking.

For example in some variations, the catheter may be formed of a tubular body that includes one or more cut-out kerfs forming a pattern of interlocking and alternating teeth extending around the tubular body and has a, e.g., first, distal region (e.g., at or near the distal end of the catheter), extending for about 2 cm or more (e.g., 2.5 cm or more, 3 cm or more, 5 cm or more, 7.5 cm or more, 8 cm or more, 10 cm or more, 15 cm or more, etc.) and a second region proximal to the distal region that extends for 2 cm or more (e.g., 2.5 cm or more, 3 cm or more, 5 cm or more, 7.5 cm or more, 8 cm or more, 10 cm or more, 15 cm or more, 25 cm or more, etc.). The teeth of the first region (on average or individually) may have a larger tooth angle than the teeth of the second region (on average or individual). For example, the teeth of the first region may have a tooth angle (in some variations an average tooth angle, in some variations a maximum tooth angle, in some variations a minimum tooth angle, in some variations a median tooth angle, etc.) of between about 61 degrees to 84 degrees (e.g., 63 degrees to 82 degrees, 64 degrees to 84 degrees, etc., 61 degrees or more, 62 degrees or more, 63 degrees or more, 64 degrees or more, 65 degrees or more, 66 degrees or more, etc.). The teeth of the second region may have a tooth angle (in some variations an average tooth angle, in some variations a maximum tooth angle, in some variations a minimum tooth angle, in some variations a median tooth angle, etc.) of between about 30 degrees to 64 degrees, between about 35 degrees to 62 degrees, between about 40 degrees to 60 degrees, about 58 degrees, etc.). At the lower tooth angle (e.g., about 45 degrees, about 48 degrees, about 50 degrees, about 55 degrees, about 58 degrees, etc.) with a 0.001" kerf, the device may be configured to have an additional linear expansion of 0.002" for each mating set of teeth. This configuration may be particularly helpful when the catheter is configured so that the second (more proximal region) has a larger locking diameter as compared to the distal end region (e.g., which may keep the catheter from prolapsing). At the larger tooth angles of the distal end of the device, e.g., having a tooth angle of about 78 degrees, with a 0.001" kerf, the distal region of the device has an additional linear expansion of about 0.005" for each mating set of teeth, leading to greater flexibility at the distal end region. Although the tooth angle of the distal end of the device may be as low as 40 or even 30 degrees in some variations, as these angles get smaller, less teeth may fit around the diameter, which, while increasing smoothness, may weaken the device and allow more loads to be concentrated on individual teeth potentially weakening the construct. Thus, in general, lower amounts of expansion between teeth of the cut-out kerf pattern may improve surface smoothness. Higher tooth angles may therefore be best utilized at the distal end of the catheter. As the tooth angle gets higher, the tooth height may need to increase to have a reasonable amount of tooth engagement (e.g., along the engagement surface). As the angle gets even larger, the tooth height may increase more, which may increases the required pitch and minimum bend diameter. Also, the teeth may be more likely to wedge together as this angle gets larger.

The pitch distance may reflect the tooth height, and may impact smoothness and flexibility. As the pitch gets smaller, the tooth height may be reduced; reducing the pitch typically requires a smaller tooth height. Higher pitch distances may therefore be used in regions having a larger bend radius/bend diameter (the bend diameter is twice the bend radius). Fewer teeth per unit length of the catheter may increase the minimum bend diameter. Similarly, lower pitch distances may be best utilized in regions having smaller bend radius/bend diameters, e.g., towards the distal end of the catheter. Lower pitch distances allow packing more teeth per unit length and may permit greater linear expansion and smaller bend radii. Although the relative expansion between each tooth may be greater due to higher tooth angles, the teeth may be made shorter (resulting in a smaller pitch) to help keep the surfaces smooth.

The normalized ratio of pitch to tube diameter may be used to adjust the properties of a catheter or region of a catheter to have desired properties. For example, a pitch to tube diameter of between about 0.009 to about 0.20 (e.g., about 0.10, about 0.12, about 0.13, about 0.15, etc.) at the distal end of the catheter may result in a high flexibility, and a larger pitch to tube diameter ratio (e.g., between about 0.30 to 0.90, about 0.31 to about 0.80, about 0.33 to about 0.70, about 0.33 to about 0.50, etc.) at the more proximal region may increase the minimum bend radius and prevent prolapse in larger-diameter vessel regions (or vessel intersection regions, such as aortic regions).

For example, a bend-limited catheter device having a length extending in a long axis, the device comprising: a tubular body having one or more cut-out kerfs forming a pattern of interlocking and alternating teeth extending around the tubular body, the pattern repeating from a distal region to a proximal region of the length of the tubular body, wherein each tooth of the interlocking and alternating teeth comprises a head region that is wider than a base region, arranged so that the head regions alternate with base regions radially around the tubular body, so that the catheter bends in a direction out of a long axis of the catheter device up to a locking radius, beyond which the tubular body does not allow further bending in the direction; wherein each tooth of the interlocking and alternating teeth form a tooth angle between a line extending through a width of the head region and a line extending from the head region and the base region; further wherein a proximal portion of the pattern of interlocking and alternating teeth comprises teeth having an average tooth angle that is less than an average tooth angle of a more distal portion of the pattern of interlocking and alternating teeth.

For example, a bend-limited catheter device having a length extending in a long axis may include: a tubular body having one or more cut-out kerfs forming a pattern of interlocking and alternating teeth extending around the tubular body, the pattern repeating from a distal region to a proximal region of the length of the tubular body, wherein each tooth of the interlocking and alternating teeth comprises a head region that is wider than a base region, arranged so that the head regions alternate with base regions radially around the tubular body, so that the catheter bends in a direction out of a long axis of the catheter device up to a locking radius, beyond which the tubular body does not allow further bending in the direction; wherein each tooth of the interlocking and alternating teeth form a tooth angle between a line extending through a width of the head region and a line extending from the head region and the base region; further wherein a distal portion of the pattern of interlocking and alternating teeth comprises teeth having an average tooth angle that is greater than an average tooth angle of a more proximal portion of the pattern of interlocking and alternating teeth; and wherein the distal portion of the pattern of interlocking and alternating teeth has a pitch to tubular body diameter ratio that is less than the pitch to tubular body diameter ratio of the more proximal portion of the pattern of interlocking and alternating teeth, wherein the pitch is a distance between adjacent rows of interlocking and alternating teeth along the long axis of the tubular body.

For example, a bend-limited catheter device having a length extending in a long axis, the device comprising: a tubular body having one or more cut-out kerfs forming a pattern of interlocking and alternating keystone-shaped teeth extending around the tubular body, the pattern repeating from a distal region to a proximal region of the length of the tubular body, wherein each keystone-shaped tooth of the interlocking and alternating keystone-shaped teeth comprises a head region that is wider than a base region, arranged so that the head regions alternate with base regions radially around the tubular body, so that the catheter bends in a direction out of a long axis of the catheter device up to a locking radius; wherein each keystone-shaped tooth of the interlocking and alternating keystone-shaped teeth form a tooth angle between a line extending through a width of the head region and a line extending from the head region and the base region; further wherein a distal portion of the pattern of interlocking and alternating keystone-shaped teeth that extends more than 2 cm along the length of the long axis comprises keystone-shaped teeth having a tooth angle that is between 61-84 degrees, and a proximal portion of the pattern of interlocking and alternating keystone-shaped teeth that extends more than 2 cm along the length of the long axis comprises keystone-shaped teeth having a tooth angle that is between 30 to 60 degrees; and wherein the distal portion of the pattern of interlocking and alternating keystone-shaped teeth has a pitch to tubular body diameter ratio that is between 0.09 and 0.30 and a pitch to tubular body diameter ratio of the more proximal portion of the pattern of interlocking and alternating keystone-shaped teeth is between 0.30 and 0.90, wherein pitch is a distance between adjacent rows of interlocking and alternating teeth along the long axis of the tubular body and the tubular body diameter is the diameter of the tubular body transverse to the adjacent rows of interlocking and alternating teeth.

The distal portion of the pattern of interlocking and alternating teeth may be configured to expand from a compressed elongate length by between about 0.005 inches and 0.085 inches per every 0.1 inch of the length of the pattern. Further, the proximal portion may be configured to expand from a compressed elongate length by less than the distal portion of the pattern of interlocking and alternating teeth.

The distal portion may be immediately adjacent to the proximal portion or may be separated from the proximal portion by a spacing region (e.g., a transition region). One or more additional portions or region, having different properties, including different pattern(s) of interlocking and alternating teeth, may be on the elongate body, including proximal to the proximal region.

As mentioned above, the distal portion of the pattern of interlocking and alternating keystone-shaped teeth may extends 2 cm or more along the length of the long axis (e.g., about 4 cm or more, about 5 cm or more, about 6 cm or more, about 10 cm or more, etc.). The proximal portion of the pattern of interlocking and alternating keystone-shaped teeth may extend 2 cm or more (e.g., 3 cm or more, 4 cm or more, 5 cm or more, 10 cm or more, etc.) the length of the long axis.

The distal portion of the pattern of interlocking and alternating teeth may have a pitch to tubular body diameter ratio that is between, e.g., 0.09 and 0.30 and a pitch to tubular body diameter ratio of the more proximal portion of the pattern of interlocking and alternating keystone-shaped teeth that is between, e.g., 0.30 and 0.90.

In some variations, the distal portion of the pattern of interlocking and alternating teeth may comprise 20 or more teeth per revolution around the diameter of the tubular body, and wherein the proximal portion of the pattern of interlocking and alternating teeth may comprise between 6-20 teeth per revolution around the diameter of the tubular body.

As mentioned above, the teeth may each form a keystone shape. The one or more cut-out kerfs may have a diameter of between 0.0005 and 0.002 inches (e.g., about 0.001 inches). The tubular body may comprises one or more of: steel, tungsten, and Nitinol.

Any of these devices may include a sealing material extending across the cut-out kerf, e.g., laminated to the inside and/or outside of the rigid tubular body. Any of these devices may include an inflatable balloon on the catheter.

The locking radius of the distal portion of the pattern of interlocking and alternating teeth may be more than 15% smaller than the locking radius of the proximal portion of the pattern of interlocking and alternating teeth. For example, the locking radius of the proximal portion of the pattern of interlocking and alternating teeth may be between 15 cm and 35 cm.

Also described herein are methods of using any of the devices described herein. In general, these methods typically include inserting the catheters using a guide devices (e.g., guidewire or guide catheter) within the lumen of the bend-limited catheter, which may provide sufficient stiffness so that it can be driven distally into the patient. The high flexibility of the catheter, particularly the distal end intermediate regions) may provide a high degree of tracking over the guidewire/guide catheter. Once in position, the guidance device may be removed from the lumen of the catheter, and the catheter may be advanced distally; because it is so 'floppy', particularly at the distal and intermediate region, the catheter will curve within (and in some cases against the vessel walls) and lock in place, preventing the distal end of the catheter from moving much. The catheter may bend only to the locking bend angle, at which point it will lock in position, preventing buckling and/or kickback and/or prolapse within the vessel. Thereafter, one or more tools (other catheters, scopes, etc.) may be delivered through the catheter to the target tissue at the distal end and force applied against the catheter, even in compression, may not substantially move the distal end of the catheter and/or kink or prolapse the catheter.

Thus, a method of providing catheter access to a target region of a vessel within a patient's body using any of the apparatuses described herein may include: advancing a bend-limited catheter device over a guidewire or guide catheter into the vessel until the distal end of the bend-limited catheter device is adjacent to the target region, wherein the bend-limited catheter comprises a tubular body having one or more cut-out kerfs forming a pattern of interlocking and alternating teeth extending around the tubular body, wherein each tooth of the interlocking and alternating teeth comprises a head region that is wider than a base region, arranged so that the head regions alternate with base regions radially around the tubular body, so that the tubular body bends freely in a direction out of a long axis of the catheter device up to a locking radius, beyond which the tubular body does not allow further bending in the direction; removing the guidewire at least partially out of the bend-limited catheter; and advancing the proximal end of the bend-limited catheter so that the bend-limited catheter locks within the vessel by bending to the locking radius without moving the distal end of the bend-limited catheter from the target region. Any of these methods may include positioning the guidewire or guide catheter into the vessel. Any of these methods may also include inserting a treatment device (e.g., scope, thrombecomy apparatus, stent, etc.) through the bend-limited catheter to the target region.

For example, described herein are methods of providing catheter access to a target region of a vessel within a patient's body, the method comprising: advancing a bend-limited catheter device over a guidewire or guide catheter into the vessel until the distal end of the bend-limited catheter device is adjacent to the target region, wherein the bend-limited catheter comprises a tubular body having a first region of one or more cut-out kerfs forming a pattern of interlocking and alternating keystone-shaped teeth extending around the tubular body, wherein each tooth of the interlocking and alternating keystone-shaped teeth comprises a head region that is wider than a base region, arranged so that the head regions alternate with base regions radially around the tubular body, so that the first region bends freely in a direction out of a long axis of the catheter device up to a locking radius, beyond which the tubular body does not allow further bending in the direction; removing the guidewire at least partially out of the bend-limited catheter; and advancing the proximal end of the bend-limited catheter so that the bend-limited catheter locks within the vessel by bending the first region to the locking radius without moving the distal end of the bend-limited catheter from the target region.

For example, a method of providing catheter access to a target region of a vessel within a patient's body may comprise: advancing a bend-limited catheter device over a guidewire or guide catheter into the vessel until the distal end of the bend-limited catheter device is adjacent to the target region, wherein the bend-limited catheter comprises a tubular body having a first region of one or more cut-out kerfs forming a pattern of interlocking and alternating teeth extending around the tubular body, wherein each tooth of the interlocking and alternating teeth comprises a head region that is wider than a base region, arranged so that the head regions alternate with base regions radially around the tubular body, so that the first region bends freely in a direction out of a long axis of the catheter device up to a locking radius, beyond which the tubular body does not allow further bending in the direction; removing the guidewire at least partially out of the bend-limited catheter; and advancing the proximal end of the bend-limited catheter so that the bend-limited catheter locks within the vessel by bending the first region to the locking radius without moving the distal end of the bend-limited catheter from the target region, wherein the first region of the tubular body of the bend-limited catheter bends freely with a lateral stiffness for a distal 10 cm of the catheter that is less than 50 grams in a direction out of a long axis of the catheter device up to the locking radius.

The tubular body of the bend-limited catheter may bend freely in a direction out of a long axis of the catheter device up to the locking radius of between, e.g., about 0.2 and 32 cm (e.g., about 0.2 and 30 cm, about 0.3 cm and about 29 cm, about 0.3 and about 28 cm, about 0.4 and about 27 cm, about 0.4 and about 26 cm, etc.).

The tubular body of the bend-limited catheter may bend freely with a lateral stiffness for a distal 10 cm (or more) of the catheter that is 100 grams or less (e.g., 150 g or less, 100 g or less, 75 g or less, 50 g or less, etc.) in a direction out of a long axis of the catheter device up to the locking radius. For example, the lateral stiffness of the distal 10 cm or more of the catheter may be 125 g or more (e.g., 150 g or greater, 175 g or greater, 200 g or greater, 250 g or greater, 275 g or greater, 300 g or greater, 325 g or greater, 350 g or greater, etc.) when the catheter is bent beyond the locking radius.

The pattern of interlocking and alternating teeth and the cut-out kerf may be configured so that the tubular body expands in the long axis from a compressed length to a maximally expanded length by between about 0.005 inches per every 0.1 inch of the length of the pattern of interlocking and alternating teeth and 0.085 inches per every 0.1 inch of the length of the pattern of interlocking and alternating teeth, as described above.

In any of the devices and methods described herein, the pattern of interlocking and alternating teeth may extend helically around the tubular body; alternatively the pattern may comprise a plurality of adjacent rings that extend around the tubular body.

Any of these methods may include compressing a sealing material extending across the cut-out kerf when advancing the proximal end of the bend-limited catheter to bend to the locking radius. The sealing material may prevent fluid from passing between the outside and the inside of the tubular member. The sealing material may be laminated to the rigid tubular body.

In some variations, as will be described in greater detail below, the bend-limited catheter may be a non-uniformly bend-limited catheter. Rotating the catheter from the proximal end may adjust the locking radius of the catheter and/or may otherwise assist in locking the catheter in position within the vessel.

Any of the methods described herein may include anchoring the distal end of the catheter near the target region. For example, the distal end may be anchored in position by inflating a balloon on the catheter (e.g., at or near a distal end of the catheter. In some variations, the distal end of the catheter may be held in position securely even without a separate anchor, as described above.

In general, the pattern of interlocking and alternating teeth may comprise a plurality of keystone-shaped interlocking and alternating teeth.

The bend-limited catheter apparatuses described herein may therefore freely permit bending of the catheter with very little (e.g., negligible) force, even when jacketed, until the catheter is bent to the locking bend angle, beyond which it is locked, and prevents bending. As mentioned above, in some variations, the pattern of interlocking teeth formed by the cut-out kerf(s) is configured so that one or more directions of bending has a different (e.g., smaller or larger) locking diameter and therefore locking bend angle.

For example, a non-uniformly bend-limited catheter device having a length extending in a long axis may include: a tubular body formed of a rigid material having one or more cut-out kerfs forming a pattern of interlocking and alternating teeth extending around the tubular body, wherein each tooth of the interlocking and alternating teeth each comprise a head region that is wider than a base region, arranged so that the head regions alternate with base regions radially around the tubular body, so that the tubular body bends freely out of the long axis up to a locking radius, beyond which the tubular body does not allow further bending; wherein each tooth of the interlocking and alternating teeth form a tooth angle between a line extending through a width of the head region and a line extending from the head region and the base region, further wherein the tooth angles of the interlocking and alternating teeth vary radially around the tubular body so that the locking radius of the portion of the length of the tubular body varies radially around the tubular body.

Any of the catheter features described above may be used as part of a non-uniformly bend-limited catheter.

In some variations, the tooth angles of the non-uniformly bend-limited catheter may vary between 10 degrees and 89 degrees (e.g., between 30 and 87 degrees, between 40 and 84 degrees, etc.). The pattern of interlocking and alternating teeth and the cut-out kerf may be configured so that the tubular body expands in the long axis from a compressed length to a maximally expanded length by between about 0.005 inches per every 0.1 inch of the length of the pattern of interlocking and alternating teeth and 0.085 inches per every 0.1 inch of the length of the pattern of interlocking and alternating teeth.

In any of these variations, the distance between the head region and the base region of the teeth may vary radially around the tubular body.

As mentioned above, the tubular body may comprise a metal or rigid polymeric material (e.g., one or more of: steel, tungsten, and Nitinol). The pattern of interlocking and alternating teeth may extend helically around the tubular body and/or may include a plurality of adjacent rings arranged along the length of the tubular body. Any of these devices may include a sealing material extending across the cut-out kerf, e.g., laminated to an outer, inner or both surfaces of the rigid tubular body. The sealing material may have a Shore A durometer hardness of greater than 75 (e.g., between 80 and 100), but may be relatively thin (typically thinner than the thickness of the tubular body).

As mentioned above, the teeth may be keystone-shaped teeth (e.g., may each form a keystone shape). Alternatively, in some variations, the teeth may each form one of: a keystone shape, a mushroom shape, and a T-shape.

The locking radius may be between about 0.2 cm and 32 cm (e.g., between about 0.2 cm and about 30 cm, between about 0.4 cm and about 29 cm, between about 0.5 cm and about 28 cm, etc.).

Any of the devices described herein may include a second region of the length of the tubular body that comprises a second one or more cut-out kerfs forming a second pattern of interlocking and alternating teeth extending around the tubular body, so that the second region of the tubular body bends freely out of the long axis up to a second locking radius, beyond which the tubular body does not allow further bending. One or more additional regions may also be included. The second (or more) regions may be non-uniformly bend-limited regions (e.g., having a varying bend angle and/or pitch), or they may be uniform bend-limited regions.

The locking radius of the first region may be different from the second locking radius at one more positions radially around the tubular body.

For example, a non-uniformly bend-limited catheter device having an elongate length extending in a long axis may include: a tubular body formed of a rigid material having a cut-out kerf forming a pattern of interlocking and alternating teeth extending around the tubular body, wherein the interlocking and alternating teeth each comprise a head region that is wider than a base region, arranged so that the head regions alternate with base regions radially around the tubular body; wherein the pattern of interlocking and alternating teeth and the cut-out kerf are configured so that the tubular body expands in the long axis from a compressed length to a maximally expanded length by between about 0.005 inches per every 0.1 inch of the length of the pattern of interlocking and alternating teeth and 0.085 inches per every 0.1 inch of the length of the pattern of interlocking and alternating teeth, so that the tubular body bends freely out of the long axis up to a locking radius, beyond which the tubular body does not allow further bending; further wherein each tooth of the interlocking and alternating teeth form a tooth angle between a line extending through a width of the head region and a line extending between the head region and the base region, wherein the tooth angles of the interlocking and alternating teeth vary radially around the perimeter of the tubular body, so that the locking radius varies around the perimeter of the tubular body; and a sealing material extending across the cut-out kerf.

As mentioned above, the distance between the head region and the base region of the teeth may vary radially around the tubular body. The device may include a second region of the length of the tubular body that comprises a second one or more cut-out kerfs forming a second pattern of interlocking and alternating teeth extending around the tubular body, so that the second region of the tubular body bends freely out of the long axis up to a second locking radius, beyond which the tubular body does not allow further bending.

The first locking radius may be different from the second locking radius at one more positions radially around the tubular body.

For example, a non-uniformly bend-limited catheter device having an elongate length extending in a long axis may include: a tubular body formed of a rigid material having a cut-out kerf forming a pattern of interlocking and alternating teeth extending around the tubular body, wherein the interlocking and alternating teeth each comprise a keystone shape having a flattened head region that is wider than a base region, arranged so that the flattened head regions alternate with base regions radially around the tubular body; wherein the pattern of interlocking and alternating teeth and the cut-out kerf are configured so that the tubular body bends freely out of the long axis up to a locking radius, beyond which the tubular body does not allow further bending; further wherein each tooth of the interlocking and alternating teeth form a tooth angle between a line extending through a width of the flattened head region and a line extending between the flattened head region and the base region, wherein the tooth angles of the interlocking and alternating teeth vary radially around the perimeter of the tubular body, so that the locking radius varies around the perimeter of the tubular body; and a sealing material extending across the cut-out kerf.

Also described herein are methods of providing catheter access to a target region of a vessel within a patient's body using any of the non-uniformly bend-limited catheters described above. For example, a method may include any of the steps described above for use with a bend-limited catheter but may further include rotating the proximal end of the catheter before or during the application of force to advance the proximal end of the catheter after removing the guide wire/guide catheter. This may allow the user to select or otherwise control the bend angle of the catheter apparatus in the lumen of the patient's body by orienting the non-uniformly bend-limited catheter so that the device preferentially bends in the selected direction out of the long axis (where the locking angle varies along the radial orientation of the device). The user may feel, via tactile feedback, the locking position of the catheter within the vessel, e.g., by feeling resistance to bending when advancing the catheter distally, as described.

For example, a method may include advancing a non-uniformly bend-limited catheter device over a guidewire or guide catheter into the vessel until the distal end of the bend-limited catheter device is adjacent to the target region, wherein the non-uniformly bend-limited catheter comprises a tubular body having one or more cut-out kerfs forming a pattern of interlocking and alternating teeth extending around the tubular body, wherein each tooth of the interlocking and alternating teeth comprises a head region that is wider than a base region, arranged so that the head regions alternate with base regions radially around the tubular body, so that the tubular body bends in a direction out of a long axis of the catheter device up to a locking radius, beyond which the tubular body does not allow further bending in the direction; rotating the bend-limited catheter to adjust the locking radius; removing the guidewire at least partially out of the bend-limited catheter; and advancing the proximal end of the bend-limited catheter so that the bend-limited catheter locks within the vessel by bending to the locking radius without moving the distal end of the bend-limited catheter from the target region.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5A is another example of a pattern (e.g., a T-shaped pattern) of interlocking and alternating teeth extending helically around the tubular body.

FIG. 5B is an enlarged view of a portion of the pattern of FIG. 5A.

FIG. 6A shows an example of a bend-limited catheter device that bends freely out of the long axis of the catheter device until reaching a locking radius (at the locking bend angle), beyond which bending is prohibited.

FIG. 7A is a table illustrating different features and variables (including ranges) that may be incorporated into any of the apparatuses and methods described herein.

FIG. 7B is a table illustrating different features and variables that may be incorporated into any of the apparatuses and methods described herein.

FIG. 8A is a graph showing an exemplary profile for cantilever bend stiffness for a catheter apparatus as described herein.

FIG. 8B illustrates one example of cantilever bend stiffness.

FIG. 9A is a graph showing an exemplary profile for Euler buckling for a catheter apparatus as described herein.

FIG. 9B illustrates one example of Euler buckling.

FIG. 10A is a graph showing an exemplary profile for torsion resistance for a catheter apparatus as described herein.

FIG. 10B illustrates one example of torsion resistance.

FIG. 11A shows an example of a catheter such as those described herein over the aortic arch, not able to make the bend into the (model of the) Brachial artery. FIG. 11B illustrates the brachial artery deforming to allow the catheter to make turn/bend. FIG. 11C illustrates an example of a catheter configured to make the turn into the Brachial artery and resist prolapse. FIG. 11D illustrates an example of a catheter apparatus configured without sufficient bend limiting (e.g., with a maximum bend angle greater than a threshold) showing the catheter apparatus making the turn into the Brachial artery, but the bend limiting does not resist prolapse into the ascending aorta.

FIG. 14A shows the apparatus in the vessel prior to locking; FIG. 14B shows an example of the same catheter apparatus after locking (by advancing distally without any guidewire or other support element within the catheter), driving against the internal lumen of the vessel.

FIG. 15A shows the apparatus in the vessel prior to locking (able to flexibly move within the vessel, including any turns/bends). FIG. 15B shows an example of the same catheter apparatus after locking (by advancing distally without any guidewire or other support element within the catheter), driving against the internal lumen of the vessel.

FIG. 16 illustrates one example of straightening of a catheter as described herein.

FIGS. 17A-17B illustrate one example of bending/curving a catheter as described herein.

FIG. 18 illustrates one example of a catheter apparatus as described herein having two zones.

FIG. 19 is a graph illustrating anchor force in a vessel comparing a catheter apparatus as described herein with a prior art catheter.

FIGS. 20A-20B illustrate kickback that may occur in operation of a prior art catheter when compressing the prior art catheter.

in FIG. 34A the locking radius (and therefore the locking bend angle) is greater in the north direction than any other direction out of the long axis of the catheter.

DETAILED DESCRIPTION

Figure 1:
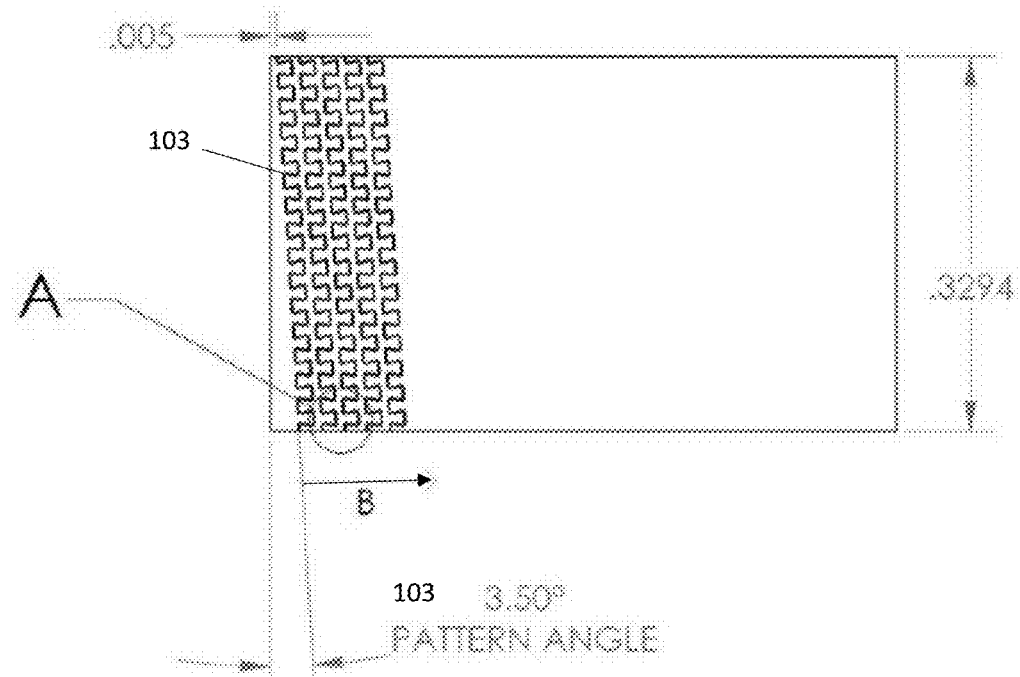
FIG. 1 is a an example of pattern (e.g., a keystone pattern) of interlocking and alternating teeth extending helically around the tubular body, wherein the interlocking teeth each comprise a head region that is wider than a base region, arranged so that the head regions alternate with base regions radially around the tubular body. The values provided for the dimensions (e.g., lengths, widths, angles, etc.) shown in this figure, and all of the following figures, unless specifically indicated otherwise, are examples only, and may be +/−1%, 2%, 5%, 10%, 15%, 20%, 25%, 30%, 50%, 75%, 100%, etc.

Described herein are bend-limited catheters (e.g., apparatuses, including devices and systems) and methods of using them. A bend-limited catheter as described herein is typically freely bendable at angles greater than the locking bend angle, e.g., when the bend radius is less than the locking bend radius; the device will typically limit or prevent bending beyond the locking bend angle. Thus, the device may be configured to bend freely in a direction out of a long axis of the catheter device without requiring a substantial amount of force, such as by applying less than a few grams of force when bending below the locking bend angle. For example, the lateral stiffness of the catheter (or of a bendable but bend-limited region of the catheter) may be less than Z grams (e.g., where Z is 150 g, 125 g, 100 g, 75 g, 50 g, etc.) when the bend angle of the region is below the bend locking angle. This may also be described as when the bend radius is greater than the locking bend radius. When freely bending, the unsupported catheter may be floppy or loose. It is generally not possible to bend the same region of the catheter more tightly than the locking bend angle (e.g., to have a bend radius less than the locking bend radius).

In general, the bend-limited catheters described herein may include one or more bend-limited regions along their length, which may have different configurations in order to have different locking bend radiuses and locking bend angles, as compared to other bend-limited regions along the length and/or as compared to other regions of the same bend-limited region around the perimeter of the catheter.

The bend-limited catheters described herein are typically formed of a tube of rigid material, such as a metal or polymeric material (e.g., stainless steel, tungsten, Nitinol, etc.) that may be cut to form the bend-limited region(s).

Thus, the tube of rigid material may include one or more cut-out kerfs forming a pattern of interlocking and alternating teeth extending around the tubular body. Each tooth of the interlocking and alternating teeth may comprises a head region (which may be flat or flattened) that is wider than a base region, arranged so that the head regions alternate with base regions radially around the tubular body. The pattern, including the width of the kerf, the shape and dimensions of the teeth and the spacing (the pitch and/or backbone region) may be configured to so that the bend-limited region is freely bendable when bent out of the long axis of the catheter (e.g., angles from 180 degrees/unbent down to the bend locking angle.

Any of these catheter devices may include a sealing material, e.g., a material having a low durometer, such as a polymeric material (e.g., silicones, elastomers, rubbers, urethanes, etc.) extending across and/or into the cut-out kerf that may prevent fluid from passing out of the lumen of the catheter. The material properties and/or the thicknesses of the sealing material may be selected so that the material (which may be a sheath, coating, etc.) does not add significant resistance to bending, particularly when the device is bent at angles greater than the locking bend angle.

The apparatuses, including in particular the bend-limited catheters, described herein may be used as part of any surgical procedure, such as minimally invasive (MI) vascular procedures. A catheter is a generally a tubular medical device that is inserted into a body cavity, duct, space, or vessel. MI catheter procedures are performed millions of times a year in the US. Bend-limited catheter may provide necessary properties when performing MI vascular procedures. Such bend-limited catheters may have a low column stiffness initially (e.g., they may bend or buckle when pushed until the locking ben angle is reached), but may be torqueable. For example, these catheters may be configured to rotate when twisted from the access point to the tip of the catheter, even over very long lengths, e.g., 0.5 to 1.5 meters. Further, these devices may be of extremely low profile, so that the device have a very thin wall thickness, providing a maximum inner diameter (ID) for MI procedures with a minimum outer diameter (e.g., a 0.001" to 0.025" thick wall). The bend-limited catheter devices described herein may typically include a bend radius that is limited or locked to reduce or prevent excursions, kinking, etc. Thus, these devices may function as a limiting endo-skeleton that creates a high-confidence, highly predictable shape when used in vascular procedure. Typically, these devices may form a locking shape shaft, so that the distal to medial shaft shape is locking (e.g., curved or straight shape locking, resulting in an increased bend stiffness at a locking bend angle). In any of these apparatuses, the locked form of the device may provide a uni-directional friction. The device may bend and lock within the vessel, so that the catheter OD engages the wall of the lumen as the device bends within the vessel; the intermediate or final catheter shaft configuration (bends) may engage with the vessel wall(s) in order to improve positioning of the catheter tip and prevent movement of the distal end of the catheter during use.

A bend-limited catheter (e.g., bend-limited support catheter) as described herein may optionally include a distal tip anchor. The catheter itself may be formed of a metallic frame (e.g., endoskeleton) that includes the cut-out kerf region forming the plurality of interlocking teeth. The catheter may also include a sealing material in, on, or over the kerf cut-out region. For example an inner and/or outer lamination, or skin, may be included.

In some variations, the bend-limited catheters described herein may include five or more components; unlike other catheters, the middle reinforcement (typically a braid or coil element) is replaced a mechanospinal element ("endoskeleton" or ES) formed of a rigid, and in some variations metallic, tube which works in unison with a tension element and distal friction element to create the properties discussed above. Thus, the tubular body is typically a rigid tubular body and may be referred to as an endoskeleton, or ES herein.

The catheters described herein may anchor the distal end of the catheter at or near a target site within the lumen of a vessel. Fixation/locking of catheter tip location relative to the access location may allow the catheter to be used to support loads, including compression loads during operation of one or more devices through the lumen of the deployed catheter without substantially displacing the catheter tip. Typically, access to vascular procedures/indications (e.g., neuro, peripheral, structural heart) are done through femoral arterial or femoral venous vessels. Vascular indications require small bore long length catheters (0.021" to 1.5" OD range by 1.5 meters long). Peripheral vascular MI procedure typically use larger shorter catheters (e.g., 0.065" to 0.183" OD). Structural heart leverages medium length catheters (e.g., 65-90 cm), femoral artery to heart (e.g., 0.065" to 0.23" OD). The bend-limited catheters described herein may be used for any of these indications.

In order to stabilize (e.g., fix or anchor) the catheter distal tip at a target location, bend-limited catheters described herein may lock the catheter tip relative to its target position. The catheter tip will resist forward or backward motion (kickback). The bend-limited catheter will therefore anchor within the conduit (blood vessel, bile duct, urinary, bowel, fallopian tubes, etc.).

The mechanospinal, column support portion of the device may be made from a metallic element laser cut to create a skeletal structure having a cut-out kerf region that is formed in to a plurality of interlocking teeth. The skeletal structure including these teeth may have features that allow for precise control of column stiffness, torque transfer, bend radius limitation, and shape locking. When the bend-limited catheter, and particularly the region including the pattern of interlocking teeth, is loaded (compression, tension, bending), it may respond by either straightening or become curved. A catheter that straightens or curves when loaded will then engage the conduit (tube) that it is located within (e.g., within the vessel). The size of the conduit and the amount of curvature of the conduit relative to the inventive catheter may affect the catheter's wall engagement, such as the tendency to anchor/resist motion. Larger conduits may benefit from greater catheter straightening or curving.

The catheters described herein may be used in any natural human or other animal conduit, such as a blood vessel, bile duct, urinary, bowel, fallopian tubes, etc.

In some variations, the catheters described herein are configured for use as one or more of: a guide catheter (e.g., 0.088" or larger diameter); a PE catheter (e.g., having about 0.031" (10 F) inner); an intermediate catheter (e.g., 0.071" ID); a structural heart catheter (e.g., having a 0.209" (16 F) size), etc.

The bend-limited structures (e.g., teeth) can be created by cutting patterns into rigid tubing. The resulting teeth structures may allow the tube to bend. Features of the kerf and/or teeth may engage to limit or reduce the amount of bending.

FIG. 1 shows an example of a pattern for, e.g., a laser cutting path into a round tube, to form one or more cut-out kerfs forming a pattern of interlocking and alternating teeth extending around the tubular body. For this example, the 0.3294 dimension is the perimeter of the tube, if cut open and flattened. The B-direction is the long axis of the tube. The pattern angle 103 is the angle relative to an axis orthogonal to the long axis. When this pattern is cut into a tube, the cut-out teeth may allow the tube to bend freely, at least to a locking radius (locking angle). In this example the teeth correspond to Keystone-shaped features (teeth) 103 that may limit the amount of bending to the locking angle (or locking radius). During bending, the aspect of the tube that is on the inside of an arc may or may not compress. Meanwhile, the aspect of the tube that is on the outside of the arc will be longer relative to the inside of the arc. This longer feature is created by movement of the teeth relative to each other. Also, these teeth limit the amount of bending, as described below.

Figure 2A:
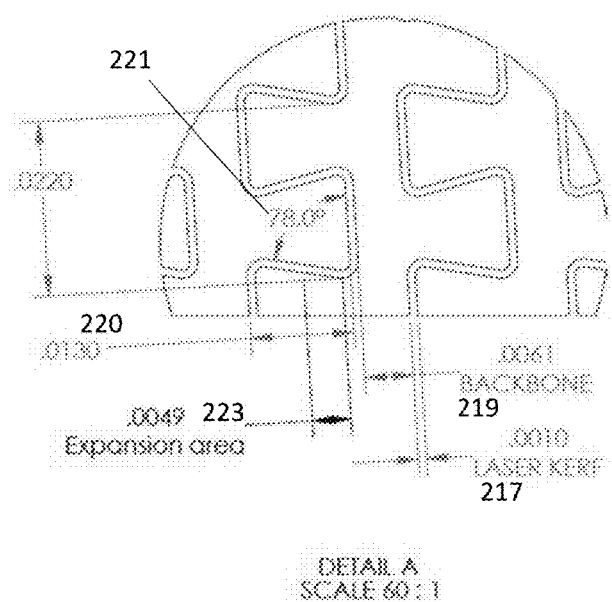
FIG. 2A in an enlarged view of a keystone-shaped pattern similar to that shown in FIG. 1.
Figure 2B:
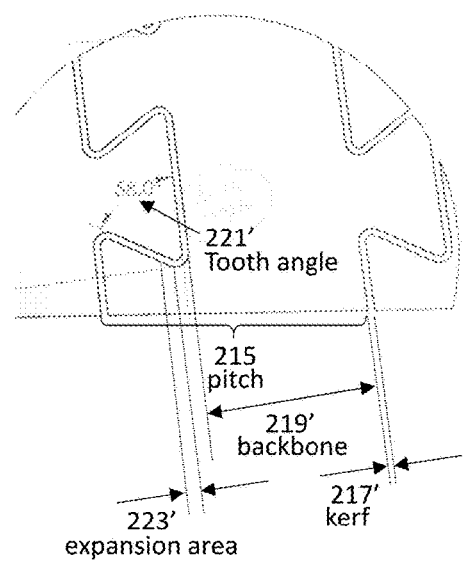
FIG. 2B is an enlarged view of another example of a keystone-shaped pattern similar to that shown in FIG. 1.

FIGS. 2A and 2B illustrate examples of laser-cut tubes having slightly different keystone-shaped patterns. In FIG. 2A, a region similar to region "B" of FIG. 1, is shown, illustrating an example of a pattern including a keystone shape (which is shown as a truncated isosceles triangle, missing the top apex) that has a tooth angle 221 (e.g., the angle between the flat region of the head region and side wall forming the base) that is about 78 degrees, while in FIG. 2B the tooth angle 221' is shown as 58 degrees. In any of the drawings, including the engineering drawings described herein, the dimensions (lengths, widths, angles, etc.) are for illustration only; actual dimensions may be varied by +/−5%, 10%, 15%, 20%, 25%, 30%, etc. of the value(s) shown).

Figure 3:
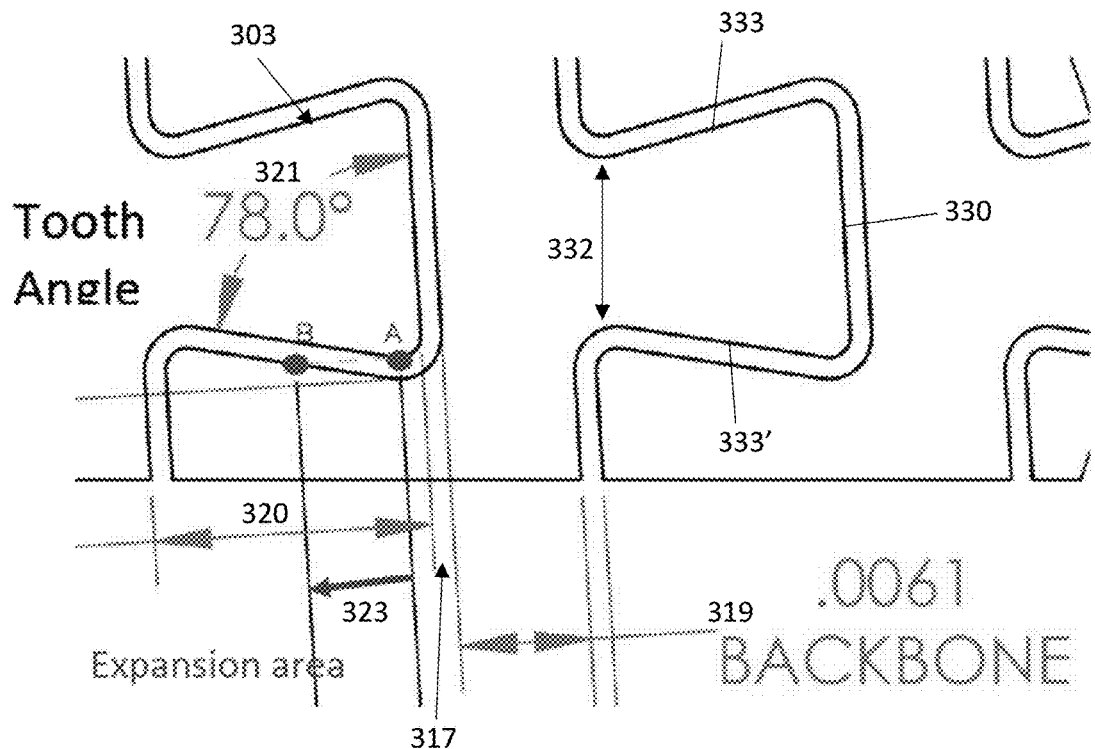
FIG. 3 is an enlarged view of a keystone-shaped pattern similar to that shown in FIG. 1.

FIGS. 2A and 2B also illustrate the spacing between the adjacent rows of a teeth, including the pitch 215, from the start of first row of teeth to the start of a second row of teeth, and the backbone 219 (the space between the end of the first row of teeth and the start of the next row of teeth along the length). The keystone shape, and particularly the kerf width 217, 217', height of the tooth 220, and the tooth angle 221, may be selected to set the locking bend angle (e.g., locking bend angle per unit of length, as described below) and/or the bend radius. FIG. 3 shows another example of an enlarged view of a cut-out kerf region forming a pattern of interlocking and alternating teeth 303 extending around the tubular body. The tooth angle 321 is shown in the enlarged figure (in this example is 78 degrees), as well as the expansion area 323 (sowing the possible expansion of the length of the catheter by moving between points A and B for this particular circumferential region of the pattern). The pitch of the teeth in this example includes the height 320 of the tooth as well as the backbone 319 (and in this example, the kerf width 317). In FIG. 3 (as well as the examples shown in FIGS. 2A-2B) the keystone-shaped teeth 403 include a flatten head region 330, a narrow-diameter base region 332, and a pair of sides 333, 333'.

Figure 4A:
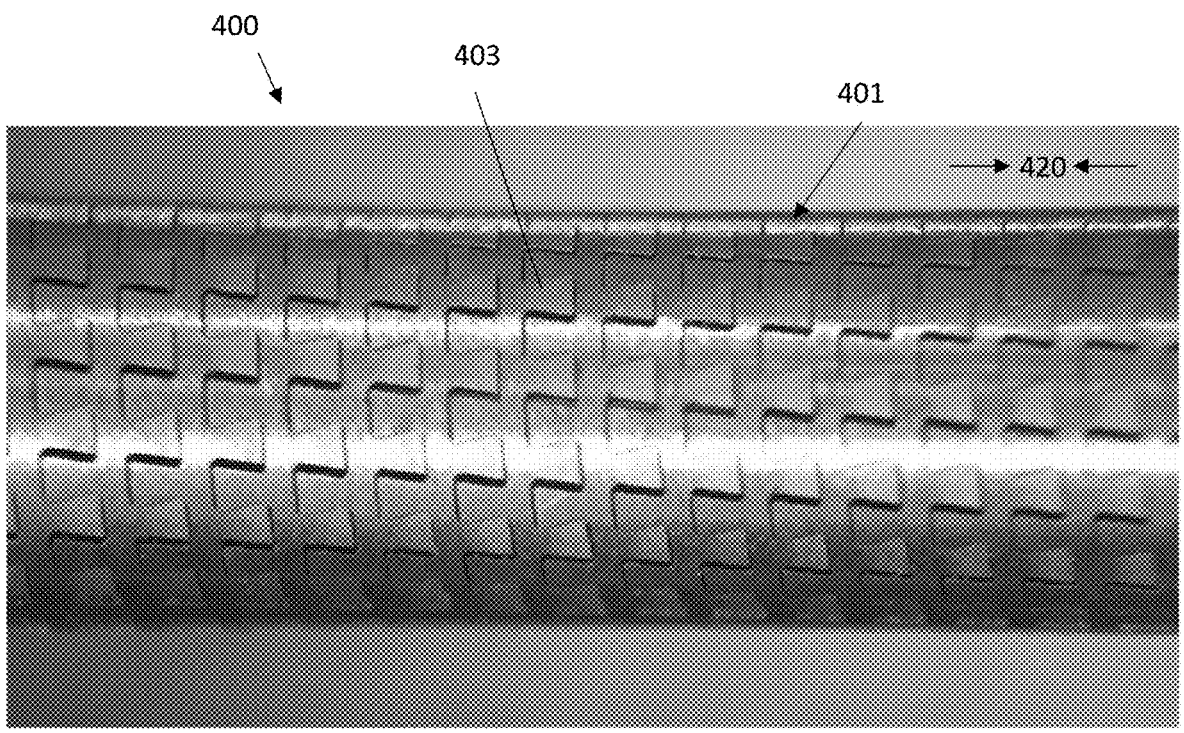
FIG. 4A is an example of one variation of a portion of a bend-limited catheter device as described herein, shown compressed along its length.
Figure 4B:
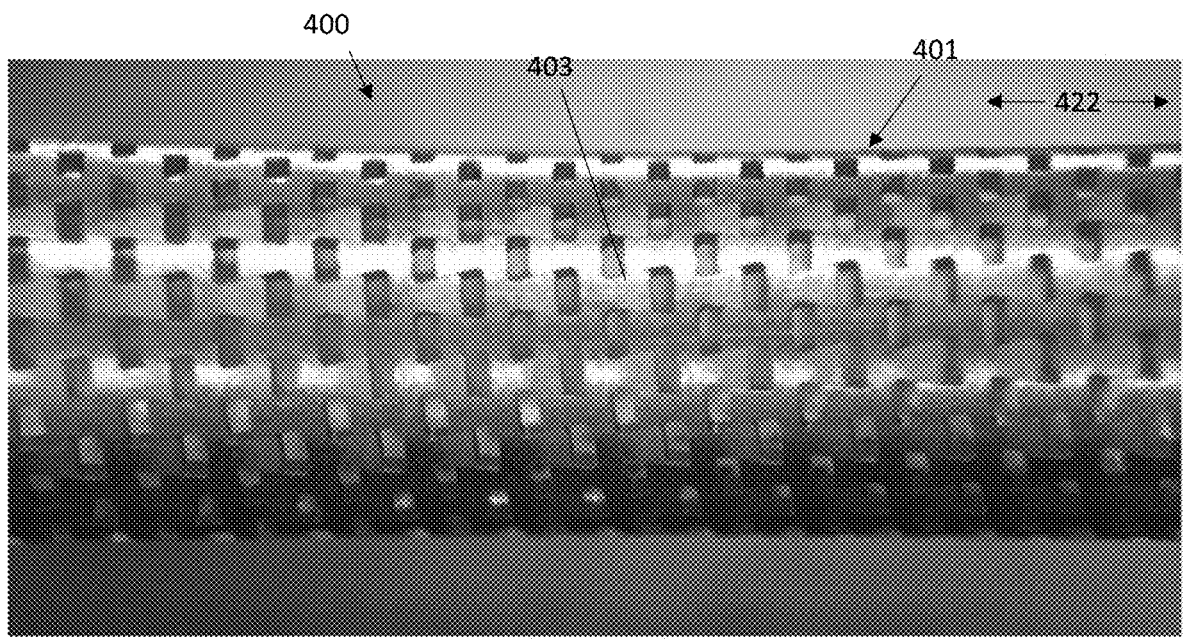
FIG. 4B shows the portion of the bend-limited catheter device of FIG. 4A expand from a compressed elongate length.
Figure 4C:
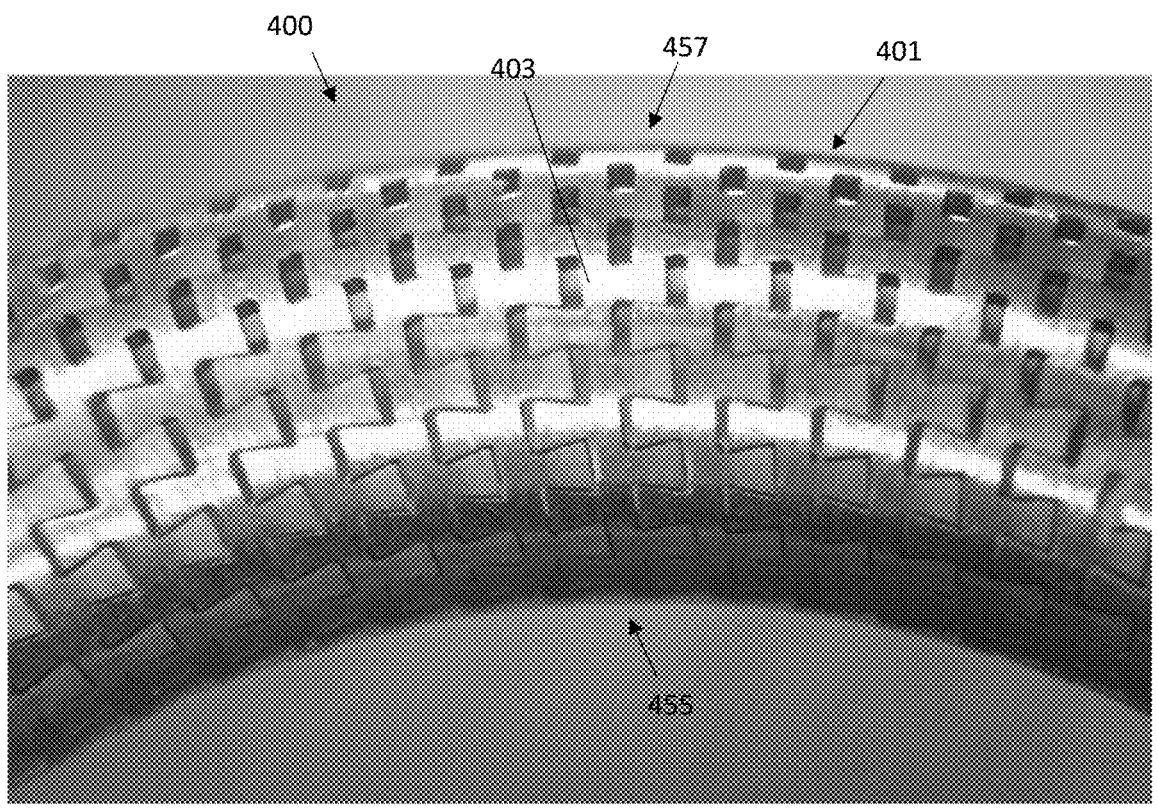
FIG. 4C shows the portion of the catheter device of FIGS. 4A and 4B bent to a locking angle.

FIGS. 4A-4C shows another example of a laser-cut tube 401 forming a bend-limited catheter device 400. In FIG. 4A, the device is shown resting, un-extended state, which is compressed in the axial direction 420. As described above, the keystone-shaped teeth 403 include a flatten head region, a narrow-diameter base region, and a pair of sides; the sides of each tooth engage and limit extension when pulled in the proximal-to distal direction, as shown in FIG. 4B. FIG. 4B shows the laser-cut tube 401 of FIG. 4A, showing the catheter in expansion 422, with the ends being pulled apart so that the pattern of interlocking and alternating teeth 403 extending around the tubular body separate. In FIG. 4B, the catheter 400 is expanded by the expansion area of each transverse ring (or spiral) of teeth in the pattern. Generally, for the catheters described herein, the expansion area is greater than the kerf diameter by greater than about 1.15×, 1.2×, 1.25×, 1.5×, 1.75×, 2×, 2.25×, 2.5×, 2.75×, 3×, 3.5×, etc. (e.g., between about 1.2× and 6×, between about 1.2× and 5.75×, between about 1.2× and 5.5×, between about 1.2× and 5.25×, between about 1.2× and 5×, between about 1.2× and 4.5×, between about 1.25× and 4.25×, between about 1.25× and 4×, between about 1.25× and 3.75×, between about 1.2 and 3.5×, etc.).

In FIG. 4C the catheter 400 is shown bending, showing the compression of adjacent keystone-shaped teeth on the inner side 455 and the expansion of keystone shapes on the outer side 457. The gaps between the keystone features close on the inside of the arc 455 while the gaps increase along the outside of the arc 457. The keystone-shaped teeth engage and limit bending along the outside of the arc. In FIGS. 4A-4C, the laser kerf is 0.001". The tooth height is 0.013" in this example. In this example, the tooth angle is somewhat high (e.g., 72-80 degrees), and the number of teeth per circumference of the tube is relatively low (e.g., 12), resulting in a surface that is less smooth than variations having a larger number of teeth/circumference.

Although the keystone-shaped teeth shown in FIGS. 1-4C may be preferred, other shapes, including more rounded keystone shapes, teardrop-shapes (and particularly teardrop shapes having a flattened head region), other such shapes may be used, including asymmetric shapes (e.g., shapes in which the tooth has multiple tooth angles, such as a first side having a tooth angle that is different from the tooth angle of the other side). For tooth shapes in which the sides are not flat or substantially straight between the head region and the base region of the tooth (e.g., in a teardrop or flatten-head teardrop shape, T-shapes, etc.) the tooth angle may be the angle of an average, mead, or median line through the side, connecting the base region to the head region.

FIGS. 5A-5B illustrate an example of a T-shaped tooth 501. In this example, the bend angle 521 is 90 degrees, as the sides 533 are perpendicular to the diameter of the head region 530 and the base region 532. The expansion area 517 shows the movement of the interlocking teeth 501. The expansion area 523 is approximately the same distance as the kerf diameter 519; the T-shaped tooth element is restricted from moving any further in the long axis than the kerf diameter. Thus, the expansion area is limited to the cut-out kerf diameter in this example. The pitch 515 show is the distance from one set of teeth to the next, along the long axis of the tube.

FIG. 6A illustrates an example of a bend-limited catheter 601 configure (at its distal end region) to bent to a full locking bend angle (β) per unit length. The locking bend angle 609 may be expressed as a locking bend angle per unit of length, also referred to herein as the minimum bend angle, wherein the length 605 is the midline 603 through the bending catheter. In some cases it may be convenient to refer to the bend angle relative to the long axis or out of the long axis of the catheter; in FIG. 6, the locking bend angle relative to the long axis 611 (or equivalently, the bend angle relative out of the long axis of the catheter) is shown as α, 610, and is 90-β (e.g., 90 minus the locking bend angle 609). The bend radius ($r_{bend}$) 607 corresponding to this minimum bend angle, for a tube having a tube diameter 613, is shown. Generally, the bend diameter ($d_{bend}$) is twice the bend radius. The bend angle and bend radius for a particular region (e.g., at a point on the length of the catheter) may be measured as from a plane transversely through the catheter at that particular region (e.g., between a first point 619 and a second point 621 at the boundaries of the particular region) and a second plane transversely though the catheter at a second spot.

Figure 6B:
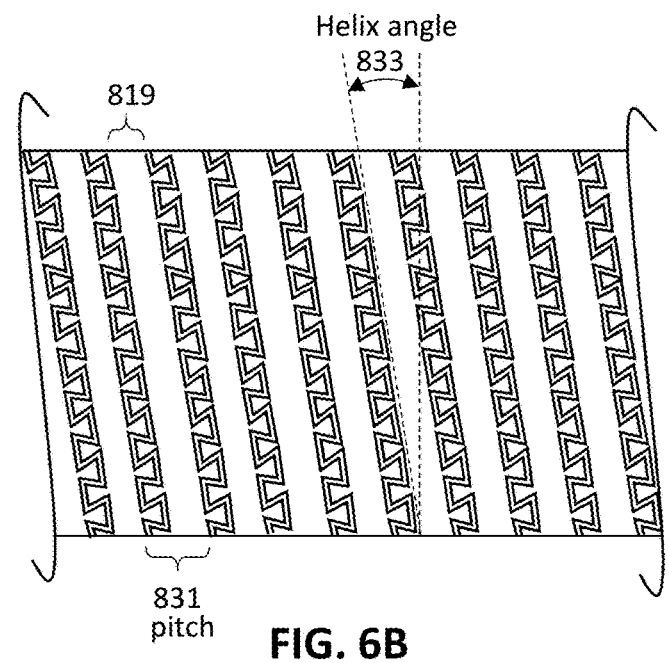
FIG. 6B is an example of portion of a tubular body of a bend-limited catheter, showing a cut-out kerf forming a pattern of interlocking and alternating teeth extending around the tubular body of the catheter.

FIG. 6B illustrates a side view of one example of a portion of a bend-limited catheter having a pattern of interlocking and alternating teeth (shown as keystone-shaped teeth) extending around the tubular body. In the portion of the pattern shown, a single cut-out kerf forms all of the interlocking and adjacent keystone-shaped teeth, which spirals helically around the tubular body. Alternatively or additionally, the pattern may form multiple separate rings (e.g., each formed by a separate cut-out kerf) that re arranged adjacent to each other (e.g., shown in FIG. 33B). The pitch 831 of teeth between the rows of teeth (in this helically-arranged example) is shown as the distance (along the long axis or length of the tube) of the tooth and the backbone region 819, which may also include the kerf diameter, as shown. The helix angle 833 between the rows are also shown.

Figure 6C:
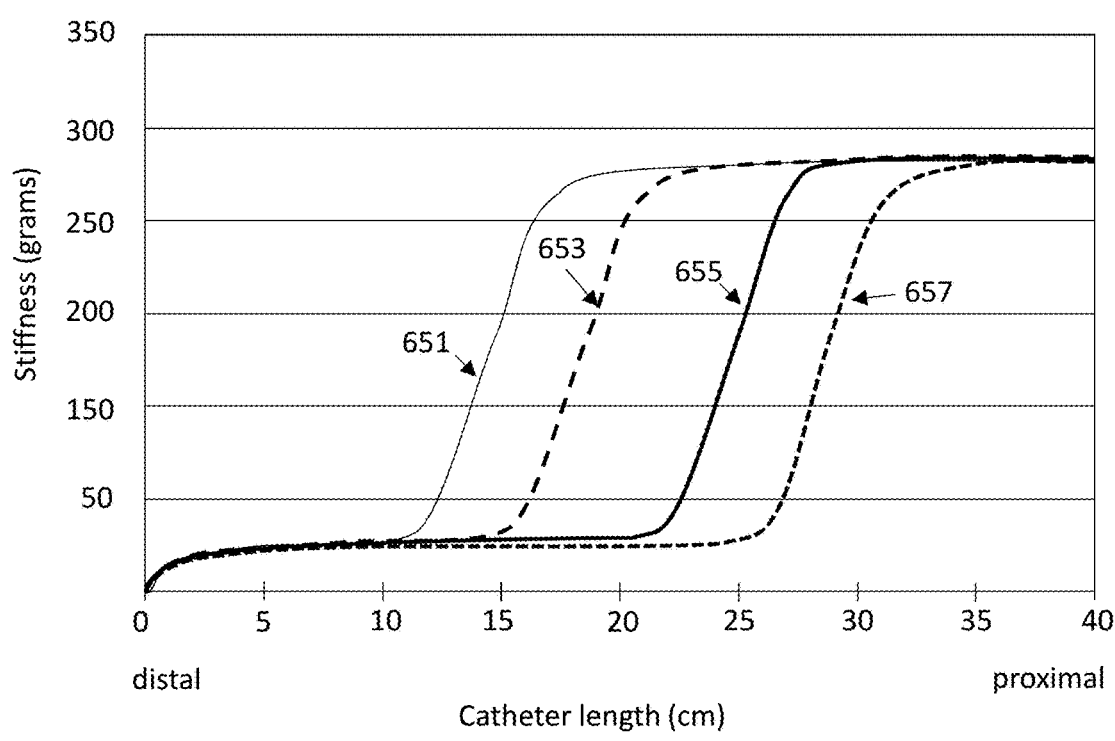
FIG. 6C is an example of a lateral stiffness profile for a series of exemplary bend-limited catheters showing the lateral stiffness along the length for the catheters. The distal ends of the catheters have a very low stiffness for bend radiuses greater than the locking bend radius (e.g., while bending at angles greater than then the locking bend angle), as shown.

The bend-limited catheters descried herein may be configured so that they are freely bendable from an unbent/straight configuration without the application of a substantial amount of force (e.g., less than 150 g, less than 125 g less than 100 g, less than 75 g, less than 50 g, etc.) to bend until reaching the locking angle. Once bent to the locking angle, the catheter may not bend further without deforming. This may be reflected in the stiffness of the catheter, so for bending at angles before reaching the locking angle the stiffness is very low over the portion of the catheter including the pattern of interlocking teeth as described above, e.g., at the distal and/or proximal regions of the catheter; more distal regions may be made stiffer (e.g., by adjusting the pattern of interlocking teeth, and/or by adding stiffing layers or elements. FIG. 6C illustrates an example of a lateral stiffness profile for a set of exemplary catheters 651, 653, 655, 657 having distal, and in some cases proximal, regions of increasing relative length that are configured as a bend-limited regions. The different lines shown represent different catheters having freely bending distal (or distal and proximal) regions of different lengths. The lateral stiffnesses shown in FIG. 6C were all estimated for the bend-limited regions at angles (relative to the long axis of the catheter) that are below the locking bend angle (e.g., at bend radiuses greater than the locking bend radius as described in FIG. 6A), so that catheter was extremely flexible in this range. Note that the different catheters illustrated may have different locking bend radiuses/different locking angles, or the same locking bending radiuses/locking angles. The stiffness may be estimated by applying force between two supports supporting a portion of the catheter to determine the force required to deflect the portion of the catheter between the supports.

A number of different variables (features) may affect performance of the devices as described herein. For example, FIGS. 7A and 7B are tables illustrating some of these. Generally, numerous variables influence the mechanical characteristics of the catheters described herein, including the patterned regions. FIGS. 7A-7B identify many of these variables, and provide some insight in how they may affect the properties of the catheter. As discussed above, these bend-limited catheter may include one or more different bend-limiting regions having a lock out angle along the length of the catheter. The bend limiting regions may be covered by an outer skin lamination (e.g., sleeve, seal, skin, cover, sheath, or the like) that may be applied on an outer, inner or both outer and inner surfaces. This lamination may create additional support while also creating spring back to original shape. As mentioned above, the cover may be particular thin, though it may have a higher durometer (e.g., durometer of greater than 75 Shore A, e.g., between about 80-100). Lamination may influence the bending shapes, bias, and limits. Some of these variables are described in FIGS. 7A-7B. Some of these variables are further described in the empirically measured graphs of FIGS. 8A-10B.

For example, the catheters described herein may be made of stiff ("stiffer") materials such as tungsten, steel (stainless steel), or other metals, including shape memory metals (Nitinol) and/or rigid polymers. The shape of the teeth (e.g., tooth angles) may be adjusted to adjust the locking angle (locking radius/locking diameter) and the expansion area per unit length. Typically larger expansion areas (e.g., at larger tooth angles, such as between 60-87 degrees) may result in a decrease in the minimum bend radius, providing an increase in the amount of bending, while lower expansion areas (e.g., at smaller tooth angles, such as between 30 and 60 degrees) may have larger minimum bend radiuses, and may decrease the amount of bending. Generally, the tooth angle may be between 1 degree and 85 degrees, e.g., between 30 degrees (so that the expansion area is greater than, e.g., 1.2×, the cut-out kerf diameter) and 87 degrees, between 35 degrees and 85 degrees, between 40 degrees and 85 degrees, between 45 degrees and 85 degrees, etc. As will be described below, in some variations the same catheter may include regions of different patterns of interlocking teeth having different properties allowing for different bending and locking angles (see, e.g., FIG. 33A, described below). The pitch may be between 0.005 and 0.3 inches; more generally, the ratio of the pitch per diameter of the tubular body (e.g., outer diameter, inner diameter or average diameter) may be between about between 0.03 and 0.90 (e.g., some regions may be between 0.03 and 0.3, or between 0.05 and 0.3, or between 0.09 and 0.3, or between 0.3 and 1, or between 0.3 and 0.95, or between 0.3 and 0.9, etc.). The total number of tooth per circumference (tooth per revolution) may be between 3 and 65, e.g., between 3 and 60, between 6 and 60, between 8 and 60, between 12 and 60, between 18 and 60, between 20 and 60, between 22 and 60, 12 or more, 14 or more 16 or more, 18 or more, 20 or more, 22 or more, etc.). The axial width of the backbone region may be between 0.002 and 0.060 inches, or may be expressed as a percent of the pitch (e.g., 60% or less, 50% or less, 40% or less, 30% or less, 25% or less, 20% or less, etc.); the lower the percent of the pitch taken by the backbone, the more teeth may be packed or the taller the teeth may be used (allowing for larger tooth angles), which may increase flexibility and/or bend angle. Other factors may include the pattern angle (e.g., the angle of the line of teeth formed by the cut-out kerf relative to the long axis of the catheter), which may be between, e.g., 1-40 degrees, and the tooth shape.

The catheters described herein are typically thin walled, but may have a relatively larger inner diameter (e.g., between 0.010 inches and 1.5 inches) when the outer diameter is approximately 0.001 inches thick (e.g., between 0.0005 and 0.005 inches).

FIGS. 8A-10B illustrate various examples of physical properties of some of the variations of the bend-limited catheters described herein. For example, a bend-limited catheters may have a cantilever bending stiffness, showing an inflection point define by the increase in bending stiffness. The bend limited catheter has locked out and bending stiffness increases significantly, as shown in FIGS. 8A-8B. FIGS. 9A-9B and 10A-10B illustrate the invention Euler buckling and Torsion Resistance characteristics, respectively. The catheters described herein include a balance of flexibility to make turns and gain access, while providing limiting bending under compression and bends.

Figure 11A:
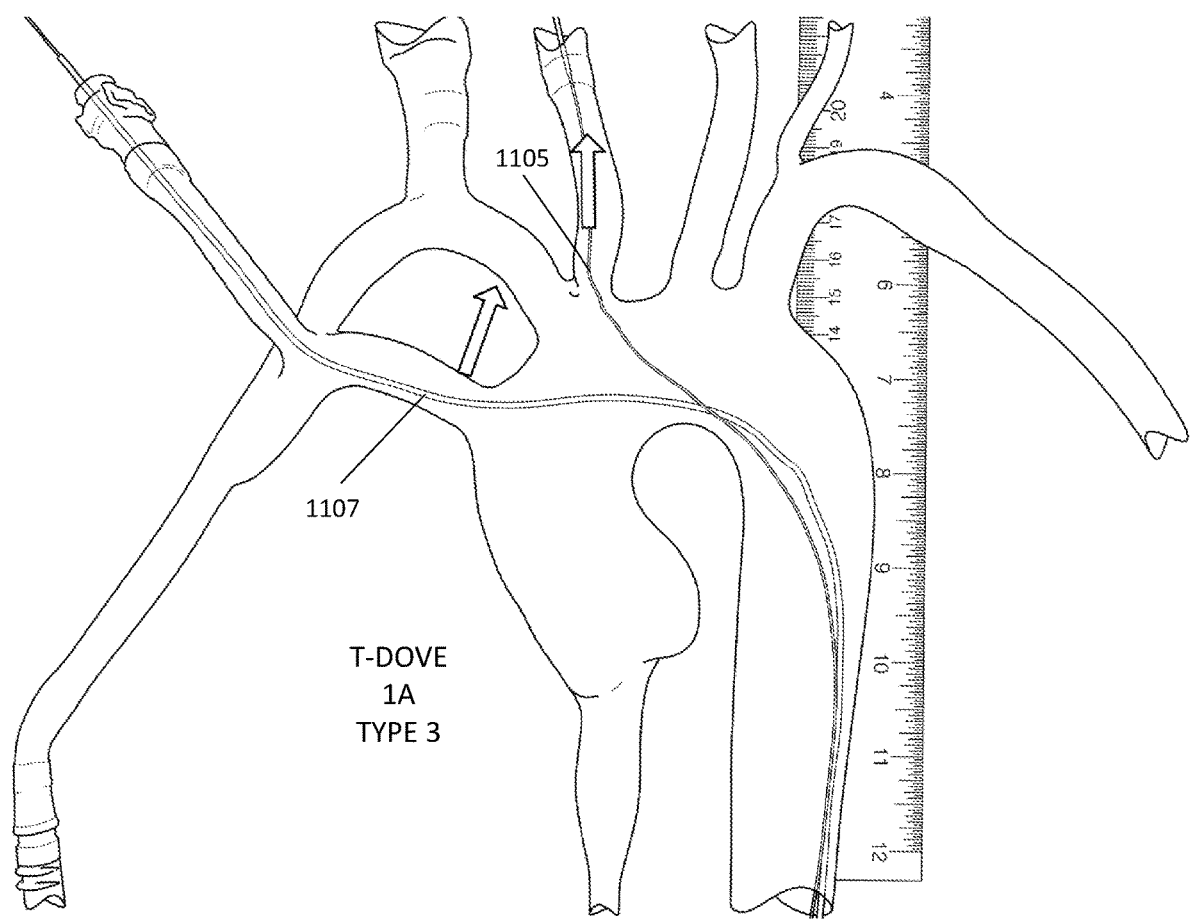
FIG. 11A-11D illustrate examples of positioning and/or operating catheters within a vasculature model (e.g., cardiac vasculature).
Figure 11B:
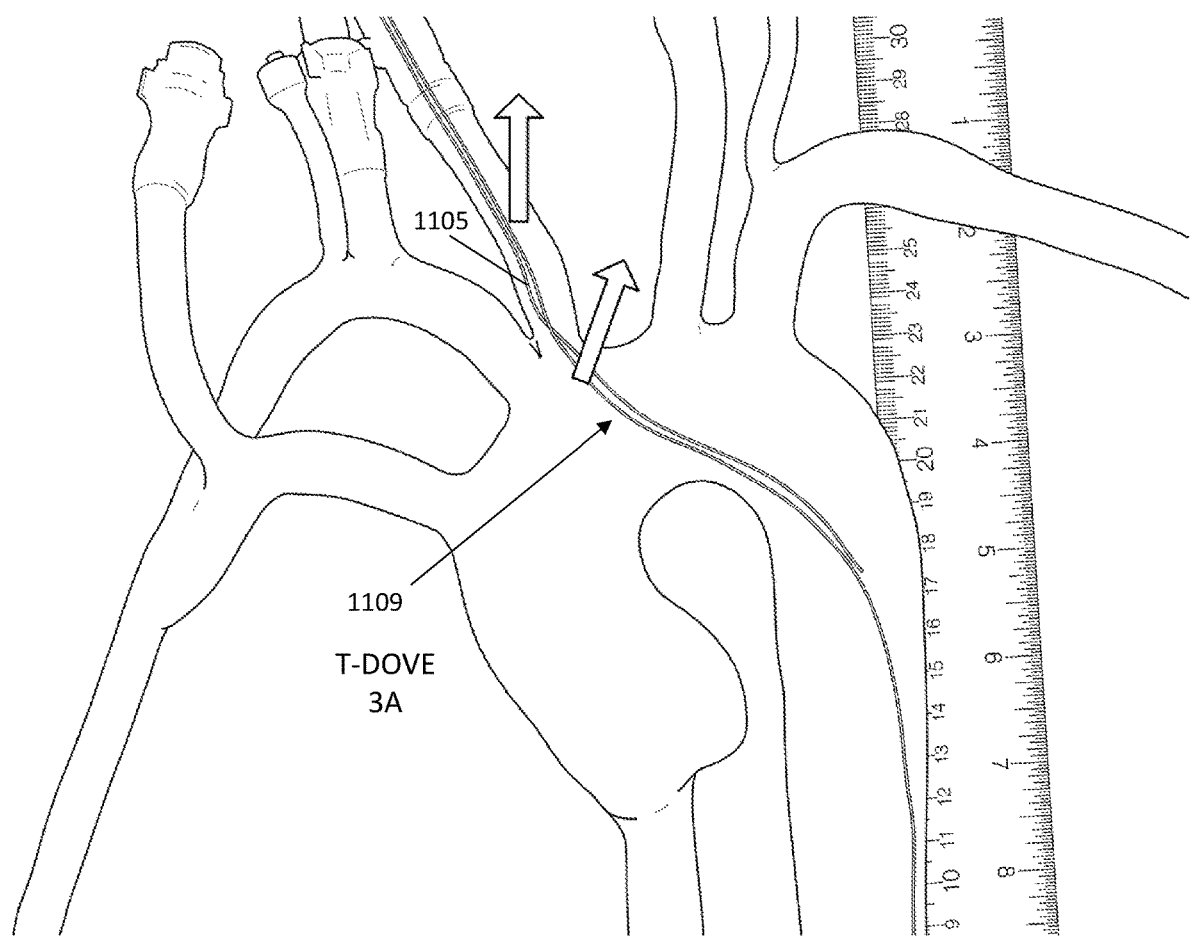
Figure 11C:
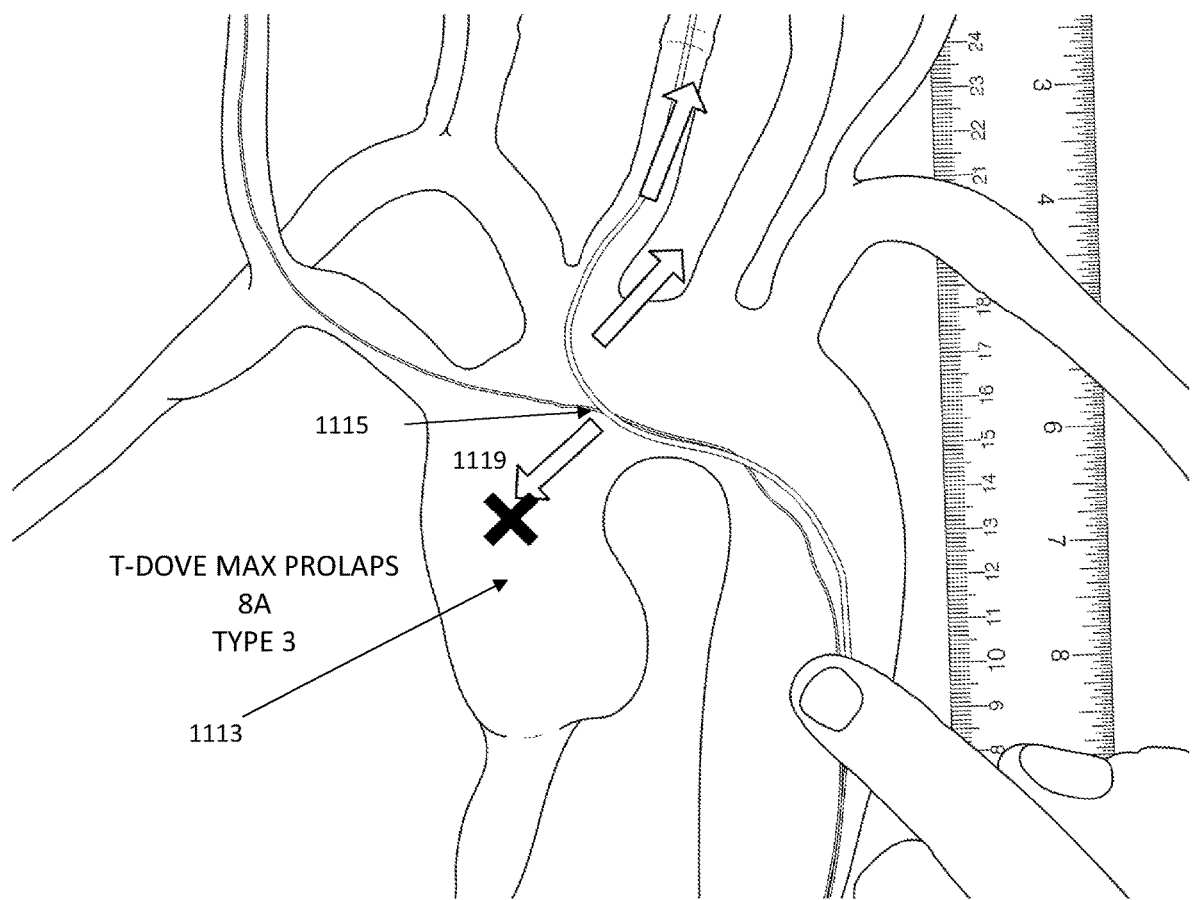
Figure 11D:
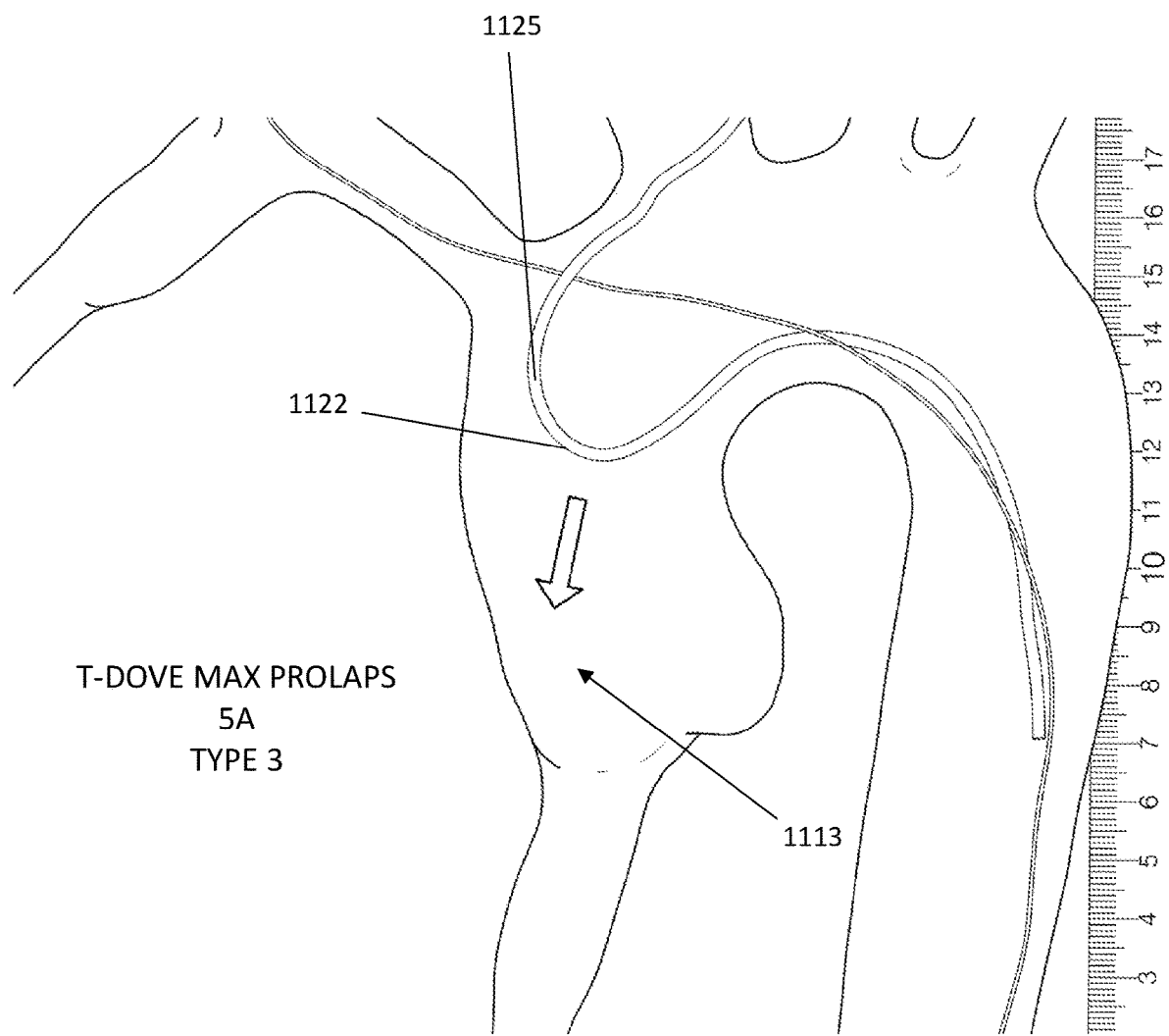

In use, the bend-limited catheters described herein may be helpful in a variety of therapeutic indications, including non-invasive and minimally-invasive surgical interventions, as they may be used in the body, including in highly tortious anatomy such as the neruovasculature, with high tracking over a guidewire, given their very low stiffness when bending out of the long axis of the catheter before reaching the locking angle (e.g., may be relatively loose and floppy) but may lock when bending out of the long axis to the locking angle, and may have a very high load capacity at the locking angle without breaking, deforming or bucking. Further, and surprisingly, driving these catheters from the proximal end (e.g., outside of the patient) may cause the catheter to lock up within the patient vessels without substantially displacing the distal end of the catheter, preventing or limiting "back out" of the catheter from the target region. For example, FIGS. 11A-11D illustrate the comparison of a bend-limited catheter within a tortious model of a patient's vessel, including an aortic arch and brachial cephalic artery. In the examples shown in FIGS. 11A and 11D the catheter used is stiffer than the bend-limited catheters shown in FIGS. 11B and 11C, and cannot access the target vessels. In FIG. 11A, the target pathway 1105 is shown by the guidewire. The catheter 1107 is not able to make the bend in the aortic arch region to track up to this target path. FIGS. 11B and 11C show how a bend-limited catheter having the right balance of flexibility and locking angle may access and provide resistance to prolapse in a tight and tortious region such as the ascending aorta and aortic valve. In FIG. 11B, the bend-limited catheter 1109 (an example having keystone-shaped teeth) tracks over the guidewire in the target path 1105, as shown. In FIG. 11C the guidewire has been removed, and a load has been applied (manually, shown by holding the distal end fixed and advancing the proximal end of the catheter, resulting in a force 1119 that would otherwise prolapse the catheter). Rather than prolapse into the aortic arch 1113, the catheter locks at the locking angle 1115 shown. FIG. 11D illustrates prolapse 1122 with a catheter 1125 that does not lock at a locking angle within the aortic arch.

Figure 12:
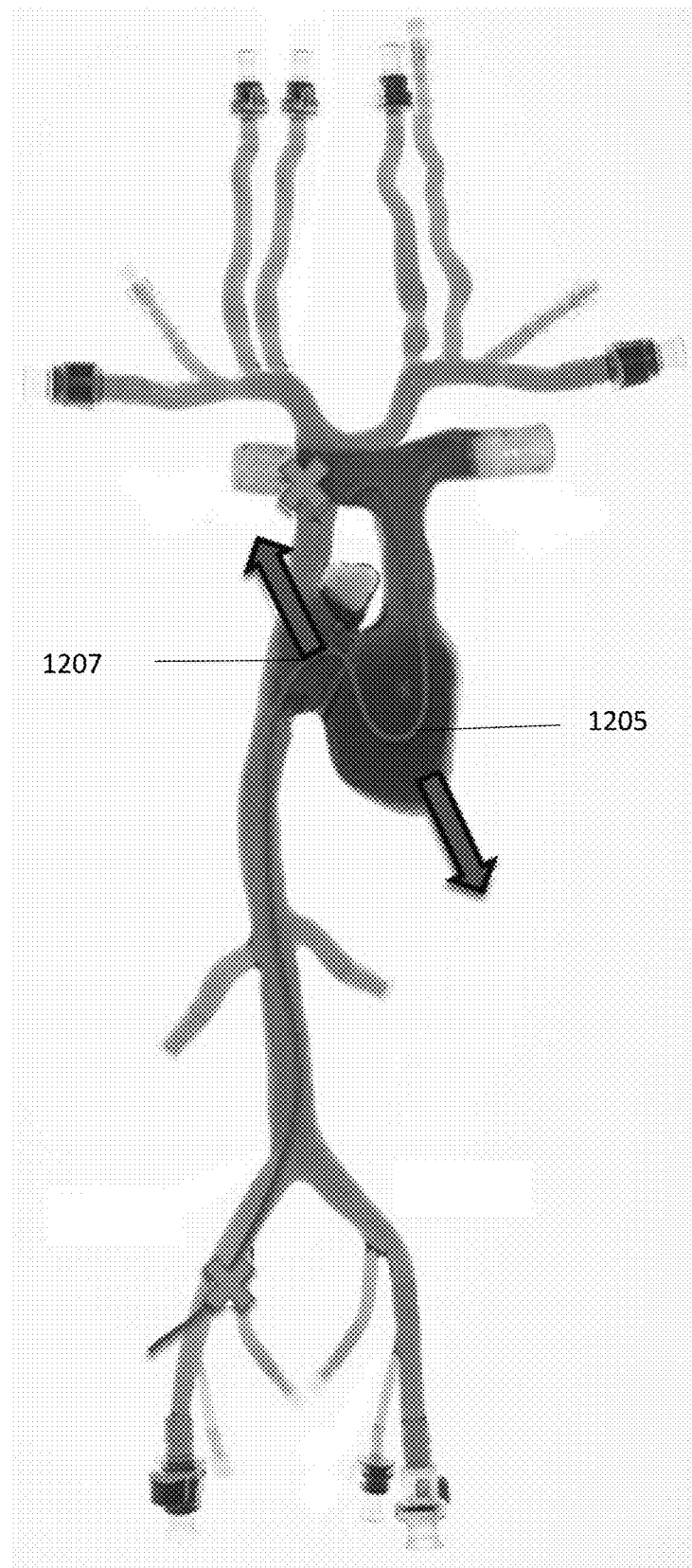
FIG. 12 illustrates one example of a pathway through the vasculature for PE treatment.
Figure 13:
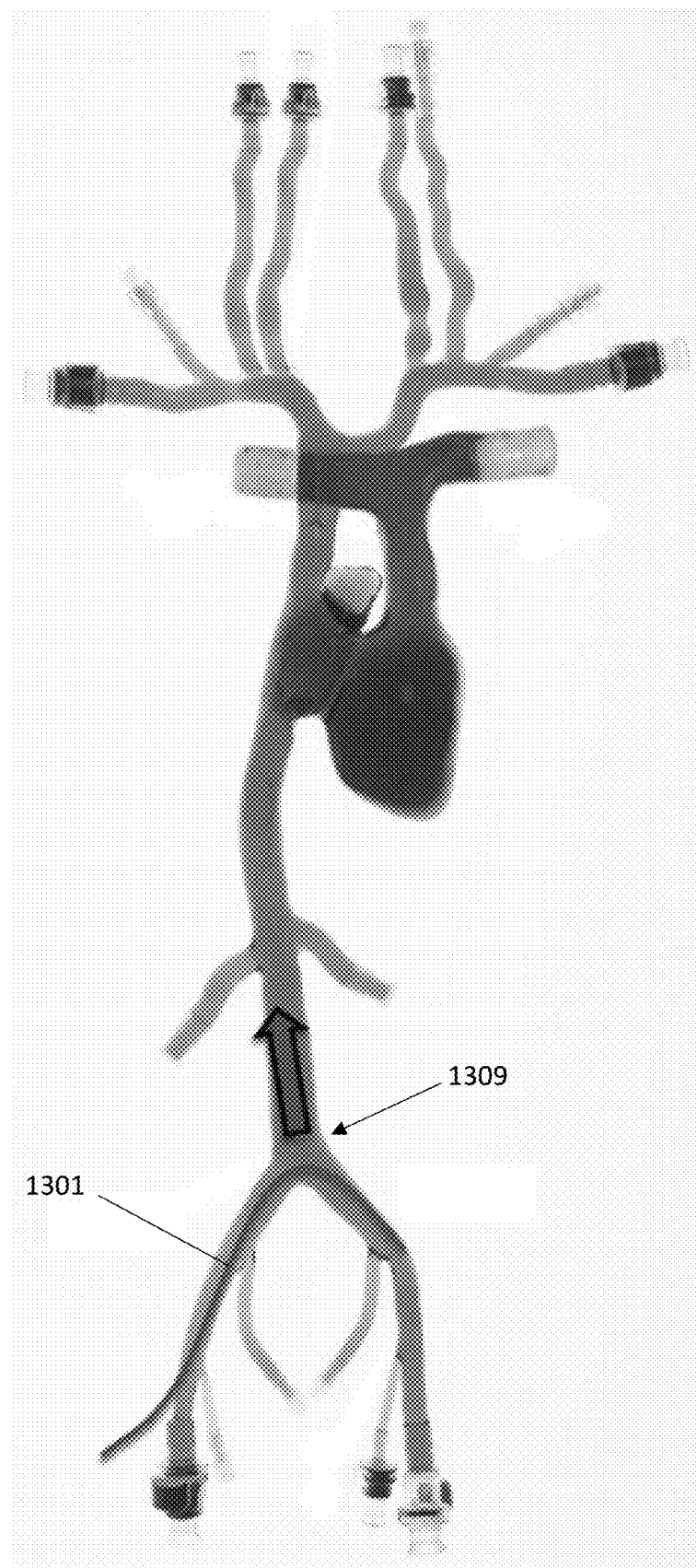
FIG. 13 illustrates one example of a catheter as described herein resisting prolapse into the descending aorta.

The bend-limited catheter described herein, including those having keystone-shaped teeth, can be tuned for use in other vessels of conduits. For instance, to reach the pulmonary artery for pulmonary embolism treatment, a catheter must be able to gain access through the venous system, through the right side of the heart. FIG. 12 shows the access path to the pulmonary artery form the right femoral vein. Arrows illustrate regions 1205, 1207 where a bend-limited catheter may include a locking angle to resist prolapse. FIG. 13 illustrates an example of a bend-limited catheter 1301 that include a locking angle sufficient to resist prolapse into the descending aorta 1309.

The bend-limited catheters in various indication will provide superior catheter support, either as a guide or stand-alone self-support due to the inventions ability to gain access, follow vessel curvature with essentially infinite column stiffness, and provide essentially infinite torqueability. The bend limited catheters described herein may therefore resist kinking, coiling and prolapse. Further, these devices may lock under load compressive load (e.g., bending stiffness increase when compressed) or by a proximal end laid out feature.

Figure 14A:
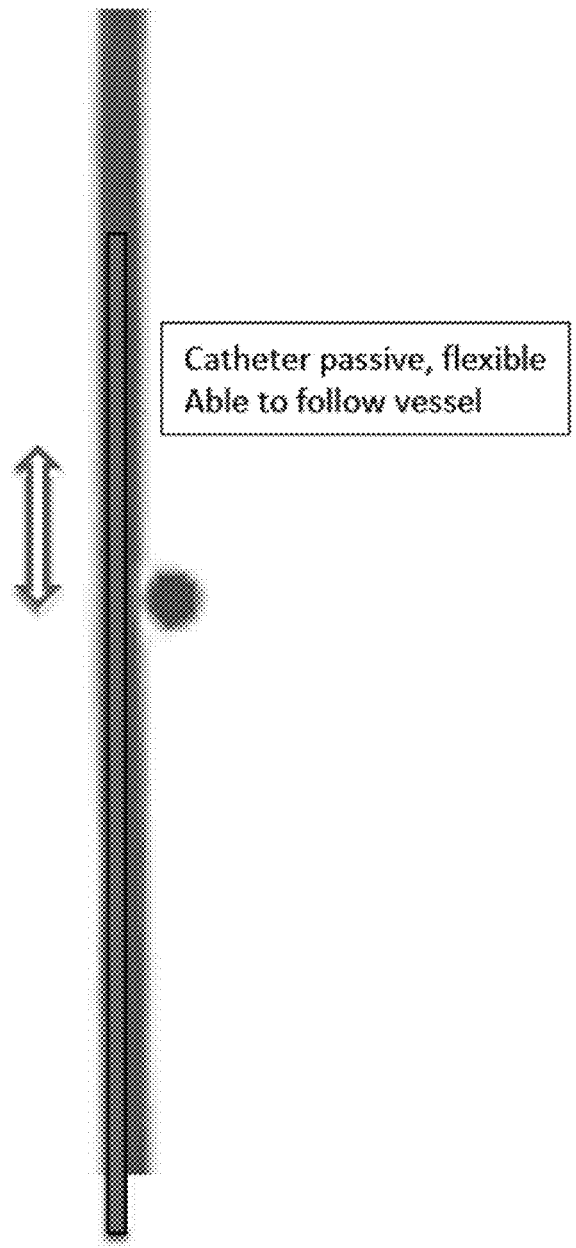
FIGS. 14A and 14B illustrate locking one example a catheter apparatus as described herein within a straight section of a vessel.
Figure 14B:
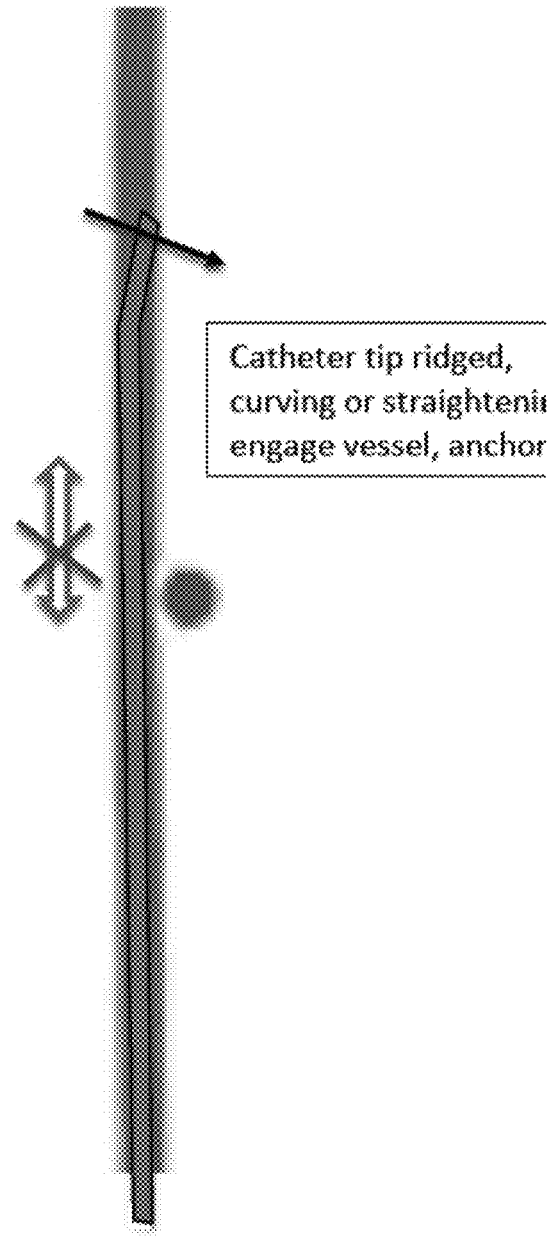

In any of the bend-limited catheters described herein the catheter may have two or more locking (bend limiting) zones or regions. In some variations, the catheter may include one or more puller threads to apply compressive force to lock the catheter. For example, the catheter may include two puller threads, as shown in FIGS. 14A-14B. FIGS. 14A-14B illustrate locking/anchoring invention in a straight section of a conduit.

Figures 15A, 15B:
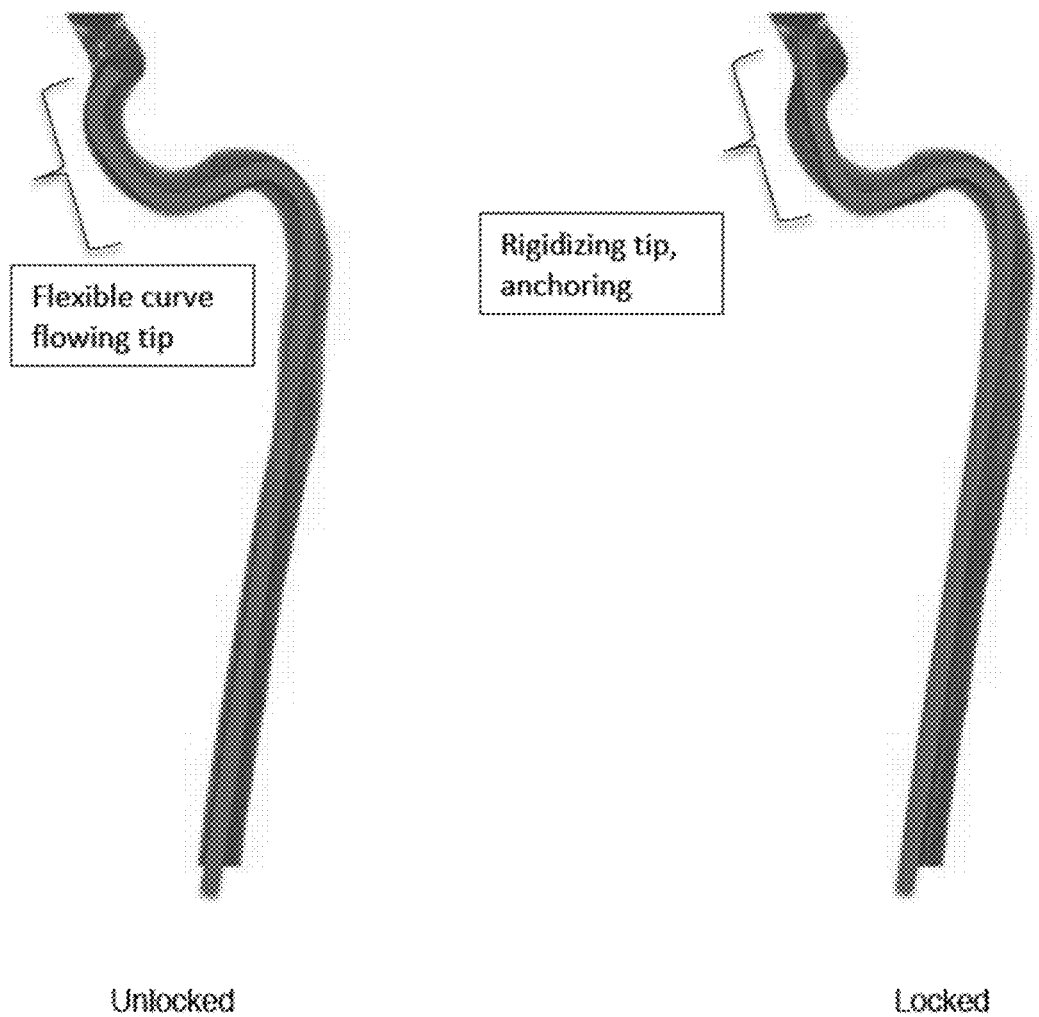
FIGS. 15A and 15B illustrate locking one example a catheter apparatus as described herein within a curved section of a vessel.

The bend-limited catheters described herein are also configured to lock against the walls of the vessel when a compressive force is applied; this locking may help anchor the devices within the vessel, and may help prevent or reduce pull back of the distal end of the device from the target region. For example, FIGS. 15A-15B illustrate locking/anchoring of a bend-limited catheter in a curved conduit (e.g., vessel, body lumen, etc.). In some variations, tip anchoring may be achieved by having a small bore pulling element attached to the catheter distal tip off its central axis. This may be called an actively actuated tip anchor. A puller wire may be placed in tension, the tip then curves until it bumps into a vessel wall of the bend limited element locks out. Alternatively the device may be locked by advancing proximally.

FIG. 16 illustrates puller along central axis. In some variations the bend-limited catheter may be biased to tend to straighten into this configuration. FIGS. 17A-17B illustrate the use of a puller 1705 that is offset from central axis to bend and/or lock a bend-limited catheter 1701. FIG. 18 illustrates a catheter 1801 having two zones with different regions of actuation (bend-limited regions, formed by two or more patterns of alternating teeth, as described above). These zones can also have different curving (or straightening) capabilities and may be (in this example) actuated by two different pull wires 1805, 1805'. Anchoring force may be measures, such as in the example shown in FIG. 19. A bend-limited catheter 1901 was compared to typical (commercially available) guide MI catheter 1905, and found to have substantially lower tip movement per compressive force. The catheters were placed in an anatomical vessel model as shown in FIGS. 20A-20B. Catheters were introduced 2001 and the location of the catheter tip was placed near a target site 2002; the catheter was placed over a guidewire or guide catheter to provide the rigidity necessary or initial placement. Once in position, the guidewire and/or guide catheter may be removed. A compression force 2007 at the tip was applied to both catheters. The force needed to move the tip backwards (kick back) was measured. Higher force is preferred (translates to more tip stability and more accurate tip location. This catheters described herein, leveraging both bend limit and tip anchor proved superior to tip movement, i.e., the tip required more force to move backwards 2005.

Figures 21A, 21B:
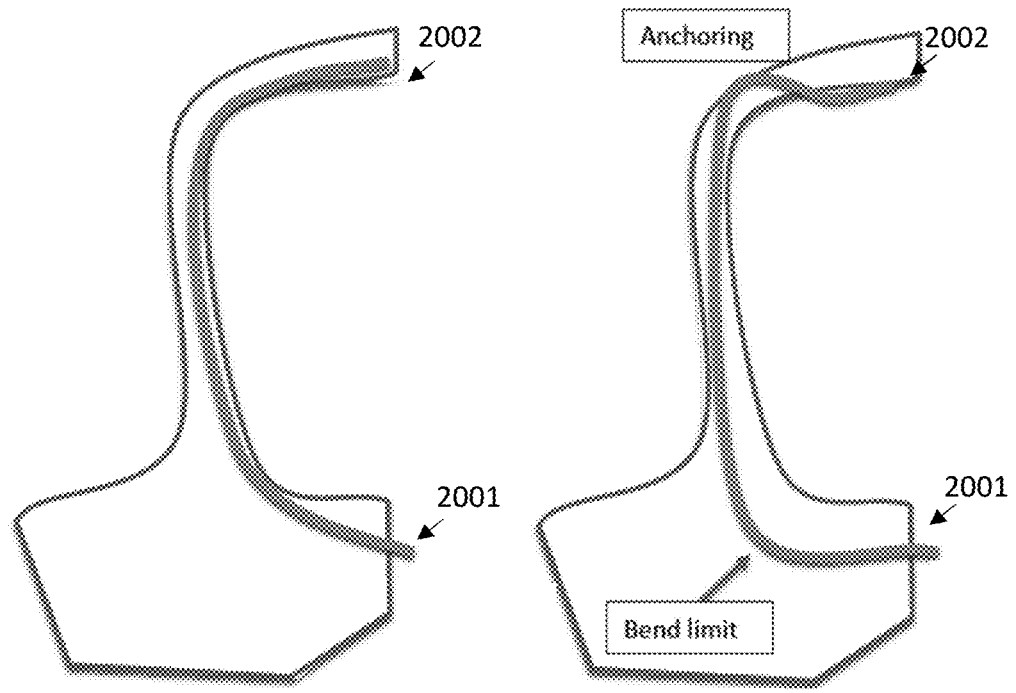
FIGS. 21A-21B illustrate catheter apparatus as described herein resisting kickback and/or buckling.

FIGS. 20A-20B shows the setup using a traditional catheter. Compressive axial load at the distal end causes kickback within the length of the catheter, resulting in distal tip backwards movement. FIGS. 21A-21B shows a bend-limited catheter as described herein having anchoring and bend-limiting features. Anchoring and bend resistance (e.g., prolapse resistance, anti-excursion) reduces or eliminates backwards movement of the distal tip, as shown. The locking feature (e.g., locking angle) of the bend-limited catheter described herein creates a stable, non-moving tip position within the vessel. Once the tip is anchored, a second catheter can be inserted, using, for example, telescopic catheters. Thus, a first bend-limited catheter may act as a guide catheter. A secondary or inner catheter may also be a bend-limited catheter.

Figure 22A:
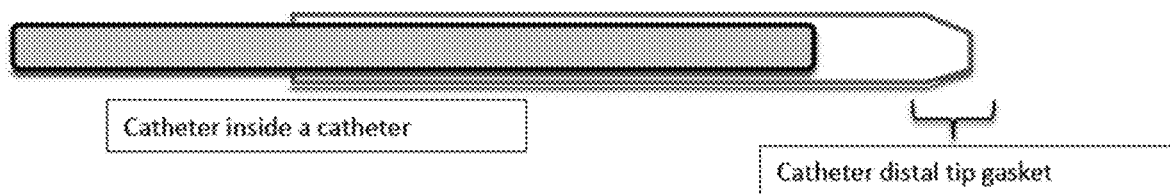
FIGS. 22A-22C illustrate one example of a catheter apparatus that is configured to lock by telescoping over a distal tip gasket.
Figure 22B:
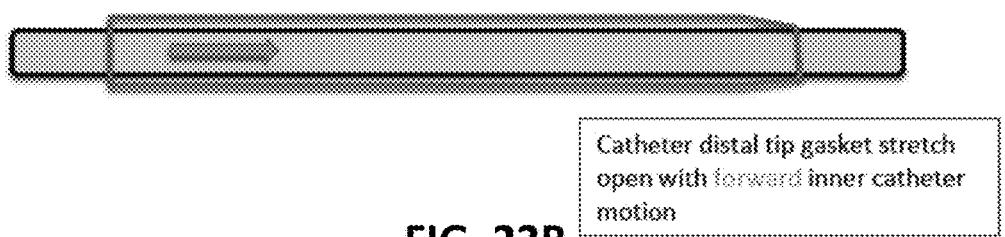
Figure 22C:
Figure 23:
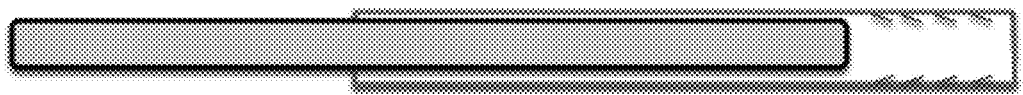
FIG. 23 is an example of a catheter apparatus configured to lock having a forward-facing element to prevent or inhibit backward movement of the inner member relative to the outer member.
Figure 24:
FIG. 24 is an example of a catheter apparatus configured to lock having an inflatable element to prevent or inhibit backward movement of the inner member relative to the outer member.

Due to the diameter ratios of the smaller catheter within the bend-limited outer catheter (large ID/OD), the locking may be less effective. However the bend-limited catheters described herein may transmit the outer bend-limited catheter's locking/anchoring to the inner bend-limited catheter's surface. This may form a telescoping catheter system, as shown in FIGS. 22A-22C. The inner (small diameter) bend-limited catheter may be actively locked to the outer bend-limited catheter, which may then produces a stable platform for use with additional components (e.g., surgical tools). This is illustrated in FIGS. 22A-22C, showing the locking nature of outer bend-limited catheter relative to the inner bend-limited catheter as a passive lock (activated by a property of the bend-limited catheter rather than requiring active engagement by a user). The outer (e.g., guide) bend-limited catheter tip may include a reverse/backward sliding element, e.g., pulling the inner bend-limited catheter backwards relative to the guide. The directional element may allow forward motion with minimal force. When the inner bend-limited catheter is pulled backward, the force increases, resisting the reverse sliding force. The reveres motion of the inner bend-limited catheter may be transferred to the outer (larger/stiffer, stronger and locked/anchored) bend-limited catheter as shown. The force transfer is to a larger outer catheter. The unidirectional tip element in this invention is accomplished using any of the examples above. FIGS. 23-24 show a locking region in the coaxial bend-limited catheter (e.g., in the inner bend-limited catheter) that may also be used.

FIG. 22A-22C illustrates a thin walled elastic tip taper section (1-10 mm long) which has a decreasing diameter (ID/OD match) to 10% smaller than the ID of a bend-limited catheter. The taping tip creates a near one-way valve. As the inner co-axial catheter advances forward through the outer catheter tip taper section, the taper stretches around the inner catheter, the taper section stretches open and the inner catheter is advanced. When the inner bend-limited catheter is puller (direction reversed), the taper grips the inner catheter and transfers load to the outer bend-limited catheter, which is locked to the vessel wall, either straightening lock or curving lock.

FIG. 23 illustrates a forward-facing filament element that resists inner bend-limited catheter movement backwards, relative to outer bend-limited catheter. Similarly, FIG. 24 illustrates an inflating balloon lock/gasket design, where the balloon squeezes the tip of the inner bend-limited catheter. This inhibits backwards movement of the inner catheter relative to the outer bend-limited catheter.

Alternatively or additionally, a stented valve design may be used. For this design, a stented valve can be used to reduce or eliminate backwards movement of the inner catheter relative to the outer catheter. For example, the stent tends to reduce in diameter when the distal aspect of the stent element is pulled towards the proximal end of the stent. This stent-like feature can be positioned at the distal end of the outer catheter, similar to previous methods shown in FIGS. 23 and 24.

The examples of methods described below illustrate the application of compression to a body of a bend-limited catheter to facilitate position and orientation locking. This may maintain the tip of the bend-limited catheter in a target distal position while the vessel is treated. For example, in some variations, the method may maintain or advance the proximal end position of the bend-limited catheter to maintain a compressed state of the bend-limited catheter; the b bend-limited catheter may be used as a guide catheter (GC), for example. In this method, the bend-limited catheter may be advanced through an optional sheath and to its targeted position by pushing on proximal end of bend-limited catheter. The bend-limited catheter can be delivered preloaded with a supportive inner dilator catheter and/or an optional guide wire to aid in delivery. Once the bend-limited catheter tip is at the target location, the dilator and/or guidewire can be optionally fully or partially removed.

The bend-limited catheter may be either maintain in the inserted position or advanced from the proximal end of the bend-limited catheter to remove slack and/or to compress the length of the bend-limited catheter. An advancing or holding force applied by the user may help force the bend-limited catheter to move into a radius-locked configuration and/or shape, as described above. The bend-limiting pattern of the interlocking teeth in the tubular body of the bend-limited catheter may make the bend-limited catheter more supportive and stiff, allowing delivery of other devices through the bend-limited catheter without kicking back and out of the patient.

The proximal end of the bend-limited catheter may be secured relative to the patient by a variety of methods so the bend-limited catheter does not uncoil from its compressed configuration. For example, the bend-limited catheter may be secured to the patient via a securement (e.g., tape, Velcro, suture, etc.), and/or the bend-limited catheter may be secured to the operating table a securement (e.g., tape, Velcro, suture, etc.). The proximal end of the bend-limited catheter may be held by hand, or by securing the bend-limited catheter through passive or active friction lock in sheath already placed in the patients' blood vessel, body or operating equipment (table, bed, etc.).

Optionally, a tightening, deflecting or compression element connected near the distal end of the bend-limited catheter may be used, including through a feature in the proximal end of the bend-limited catheter. This actuation can additionally stiffen the bend-limited catheter to create a supportive structure/tube for delivery of other devices.

In some variations the bend-limited catheter may be operated by distal end actuation to apply compression to the bend-limited catheter. For example, an advance bend-limited catheter may be positioned by pushing on proximal end of bend-limited catheter until the distal tip is at target location; a stiffening inner and/or outer member may be used, such as a guidewire. The position of the proximal end of the bend-limited catheter may be maintained relative to patient. A tightening, deflecting or compression element connected the distal end of the bend-limited catheter may be actuated through a feature in the proximal end of the bend-limited catheter, which may apply compression forces between the distal end and proximal end of bend-limited catheter, encouraging the bend-limited catheter into a radius-locked orientation/shape. The radius-locked orientation of the catheter may maintain the distal positioning and may create a more supportive structure/tube for delivery of other devices.

Figure 25A:
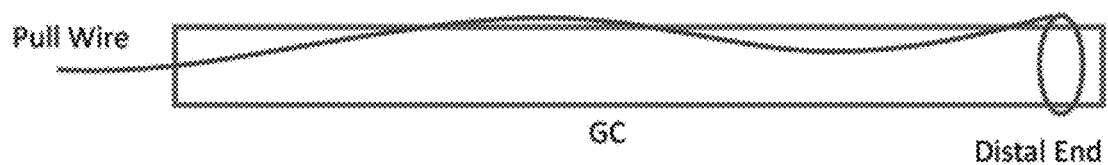
FIG. 25A is an example of a catheter apparatus as described herein including at least one pull wire (shown untensioned)
Figure 25B:
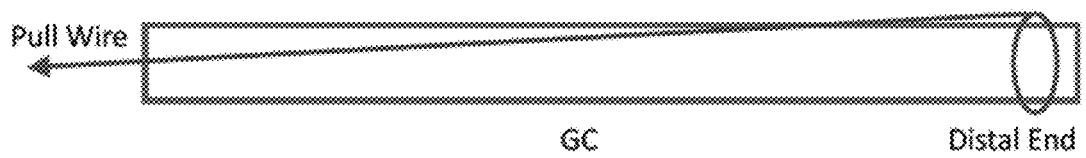
FIG. 25B shows the apparatus of FIG. 25A with the pull wire in tension.

In some variations, a pull wire may be used to apply compression to a bend-limited catheter. For example, a bend-limited catheter may be advanced into position by pushing on a proximal end until the distal tip of the bend-limited catheter is at target location (as before a stiffening member may be used). The position of the proximal end of the bend-limited catheter may be maintained relative to the patient or the proximal end may be advanced. Tension may be applied to a pull-wire coupled to the bend-limited catheter while maintaining the position of the proximal end of the bend-limited catheter relative to the patient (e.g., by pushing). The pull wire may be fixed to the distal end (or a distal end region) of the bend-limited catheter, and can be pulled from outside the patient (as shown by example in FIG. 25A). Tension on this pull-wire may apply a compression along the length of the bend-limited catheter, as shown in FIG. 25B. This compression may improve the radius-locked orientation/shape of the bend-limited catheter. The radius-locked orientation of the bend-limited catheter may maintain the distal positioning of the bend-limited catheter, allowing actuation to be more effective.

The bend-limited catheters described herein may be fabricated in a manner that modifies their properties. For example, the extension state of the bend-limited catheter during fabrication can affect the properties of the catheter, including trackability (the ability of the catheter to get to the target location), bend limiting (the ability of the catheter to resist bending and lock out in key areas), and compression resistance (the ability of the catheter to resist compression during use). The bend-limited catheters described herein typically have superior control of bend limiting and compression resistance as compared to prior art devices, which may increase the ability to maintain distal tip position during use.

The bend-limited catheters described herein may be in any of three or more different states of extension prior to (and during) the addition of sealing (e.g., lamination) materials to the inner and/or outer surfaces of the bend-limited catheter. For example, the catheter may be in a compressed, relaxed, or extended configuration (or some combination of these, or intermediate position between these, including bent/curved). This may affect the final shape set of the bend-limited catheter. The modulus of the sealing material (e.g., lamination) relative to that of the spring-like tubular body may influence the properties of the catheter.

For example, if the bend-limited catheter is laminated when compressed, the tubular body (including the pattern of interlocking teeth) may act like a coil spring in compression, being held in position by an elastic in tension. When the bend-limited catheter is laminated in a relaxed state, the tubular body and the sealing material may act like springs in unloaded states. When the bend-limited catheter is laminated in the extended state, the tubular body may act like a coil spring in tension, being held in position by a rubber tube in compression.

The amount of sealing material that protrudes into the kerf, e.g., between the laser cut edges, may also influences the properties of the catheter; this may be reflected in the thickness of the sealing material. Further, a minimal amount of sealing material within the laser cut kerf region may result when the sealing material is applied in the compressed configuration. A nominal amount of sealing material may be present in the kerf when the material is applied in the relaxed configuration. This sealing material may increase the ability of the bend-limited catheter to bend, by compressing along the inside arcs of bends.

When the sealing material is applied in the expanded configuration, a maximal amount of sealing material may be laminated into the kerf. This sealing material may further increase the ability of the bend-limited catheter to bend, by compressing along the inside arcs of bends.

Figure 26:
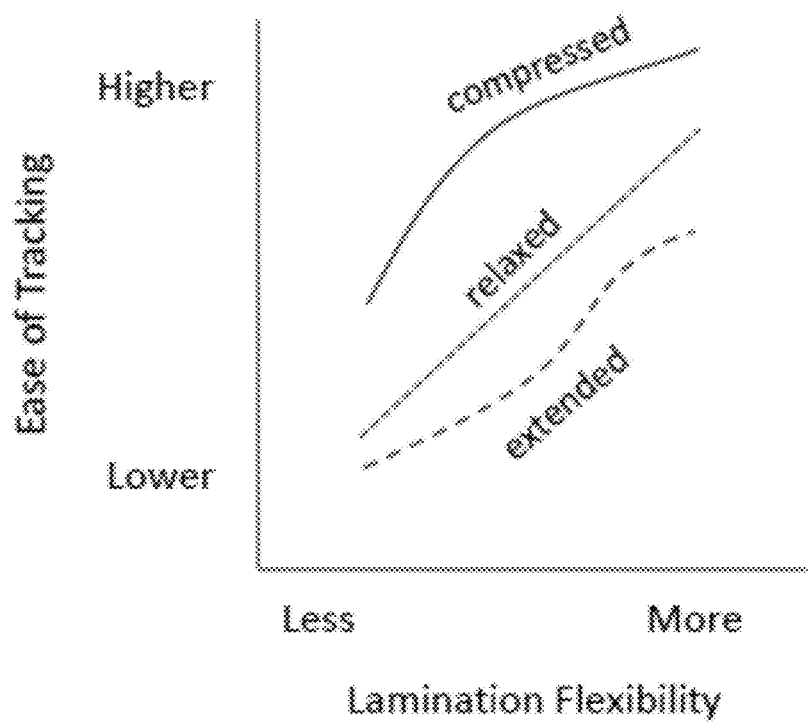
FIG. 26 is a graph illustrating how the ease of tracking the catheter apparatuses described herein can be affected by the state (compressed, relaxed, extended) of the apparatus, as compared to the flexibility of any lamination on the catheter apparatus.
Figure 27:
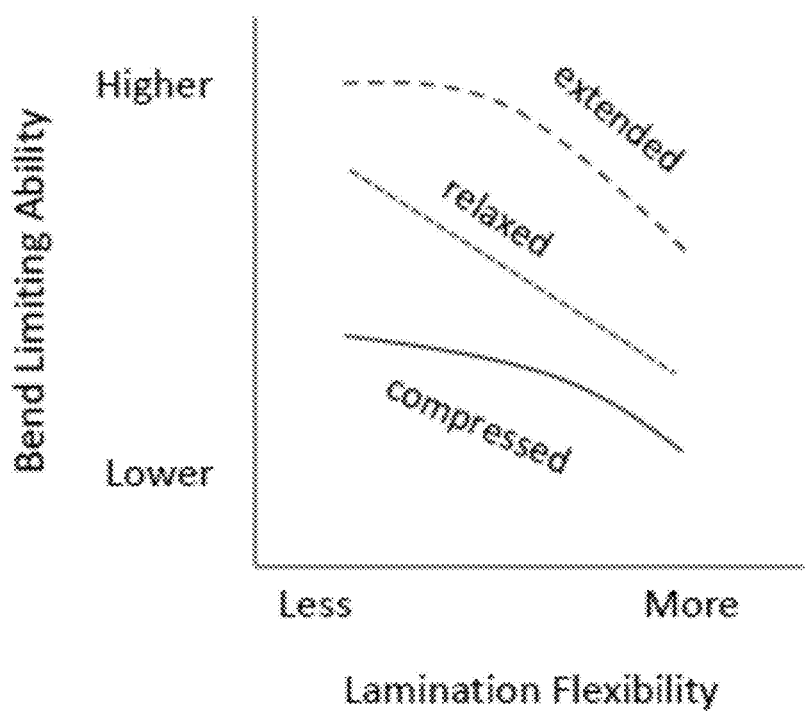
FIG. 27 is a graph illustrating how bend limiting can be affected by the state of the catheter apparatus (e.g., compressed, relaxed, extended) in a laminated catheter.
Figure 28:
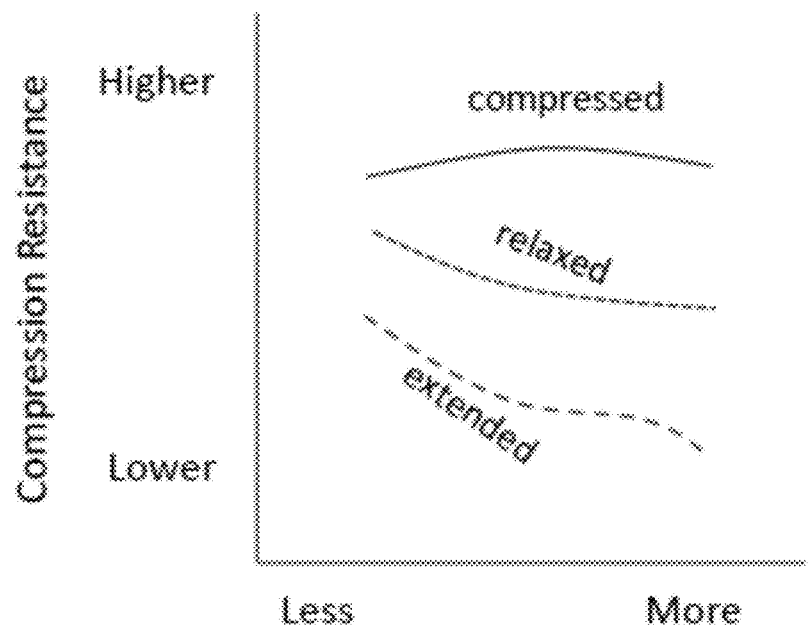
FIG. 28 illustrates how compression resistance of the catheter apparatus can be affected by the state (e.g., compressed, relaxed, extended) during in a laminated catheter.

FIGS. 26, 27 and 28 for illustrate example of the effects of applying sealing material (lamination) in various amounts within the kerf region (e.g., applying when compressed, having little material, when relaxed, having a moderate amount of material, or when expanded, having the most material). These properties may relate to one another for a particular bend-limited catheter and sealing material combination.

In some variations, a thin-wall braided tube can be positioned outside of the bend-limited catheter to provide bend limiting resistance. During catheter bending, the braided tube may increase frictional resistance against the bend-limited catheter (e.g., the tubular body), reducing the catheter's ability to lengthen along the outside aspect of the curve. This may limit bending. Variables that govern relationship include: braid material stiffness, braid material size, number of braid ends, braid angle, braid pattern, braid "wall thickness", braid inner diameter relative to the tubular body outer diameter, braid material profile (round, square, etc.). Also, a braid can be designed to have diameter "bumps" or angle changes. This facilitates focusing the bend-limited characteristics to localized regions along the bend-limited catheter. The braid can be loose outside the bend-limited catheter, within the sealing material/coating (e.g., lamination), or sandwiched in-between the sealing coating and the tubular body.

Figure 29A:
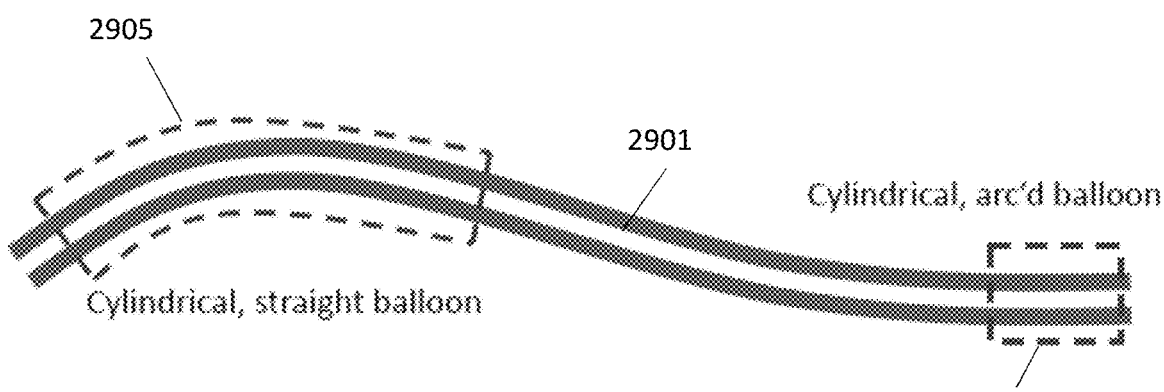
FIG. 29A schematically illustrates operation of one example of a catheter apparatus with multiple balloons, not inflated. These balloons may passively follow the geometry of catheter.
Figure 29B:
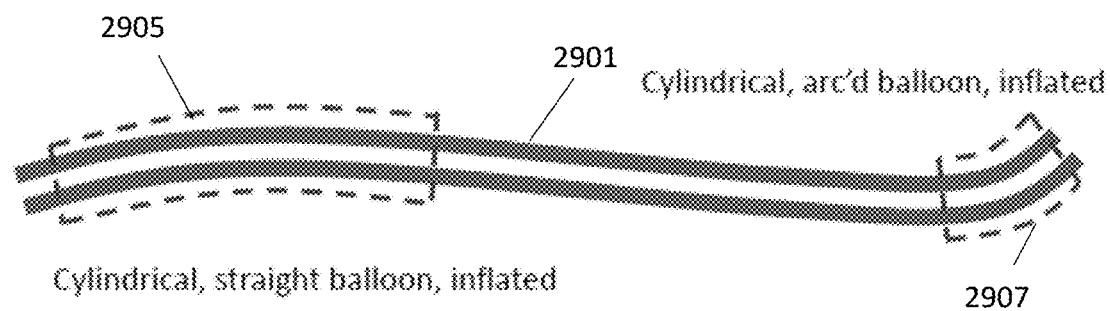
FIG. 29B shows the catheter apparatus of FIG. 29A with the balloons inflated. The longer balloon on the left encourages the catheter to straighten, while the shorter balloon on the right encourages bending.

As mentioned above, any of these devices may include a balloon that can be secured to the bend-limited catheter, e.g., on the outside of the bend-limited catheter. When filled with fluid, it may add stiffness to the catheter. This can help anchor the distal tip of the catheter in a desired location, and/or help resist bending in other locations. A balloon can be positioned along the length of the bend-limited catheter, on the inside or outside. This balloon may be positioned outside of the bend-limited catheter, or inside of the bend-limited catheter. The balloon can be in the shape of a straight tube, an arced tube, a straight line, a helix, etc. This balloon does not have to be run along the entire length of the ES, but may extend over a small region of the catheter, nor does the balloon have to be one continuous shape, but may contain multiple different shapes. Preferably, the balloon may be a tubular balloon. This balloon may be actively inflated/activated and deflated/inactivated from outside the body. FIGS. 29A-29B illustrate one example of tubular balloons 2905, 2909 over a bend-limited catheter 2901. The uninflated balloons show in FIG. 29A are shown inflated in FIG. 29B.

Figure 30:
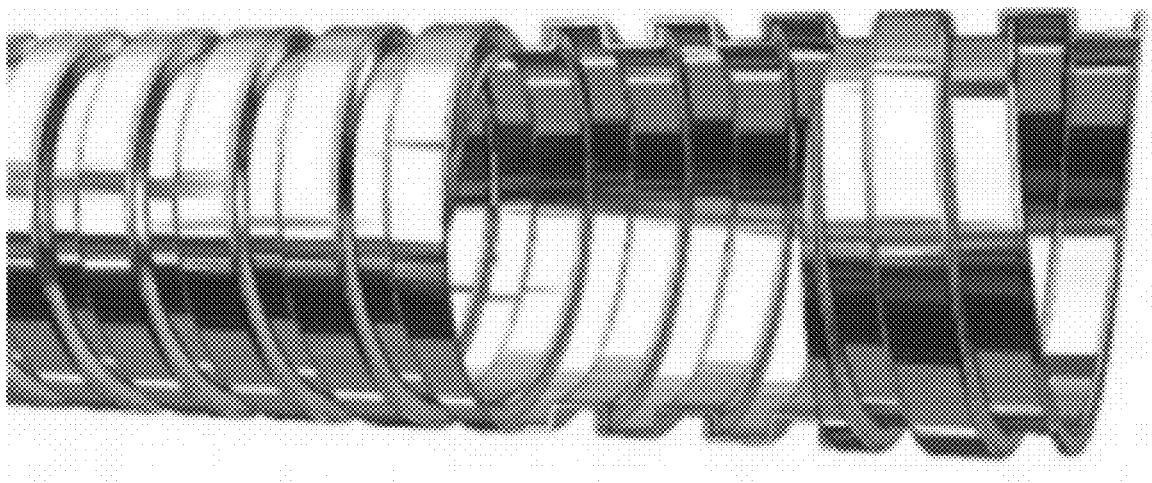
FIG. 30 shows another example of a catheter apparatus as described herein, including a cut-away region.
Figure 31:
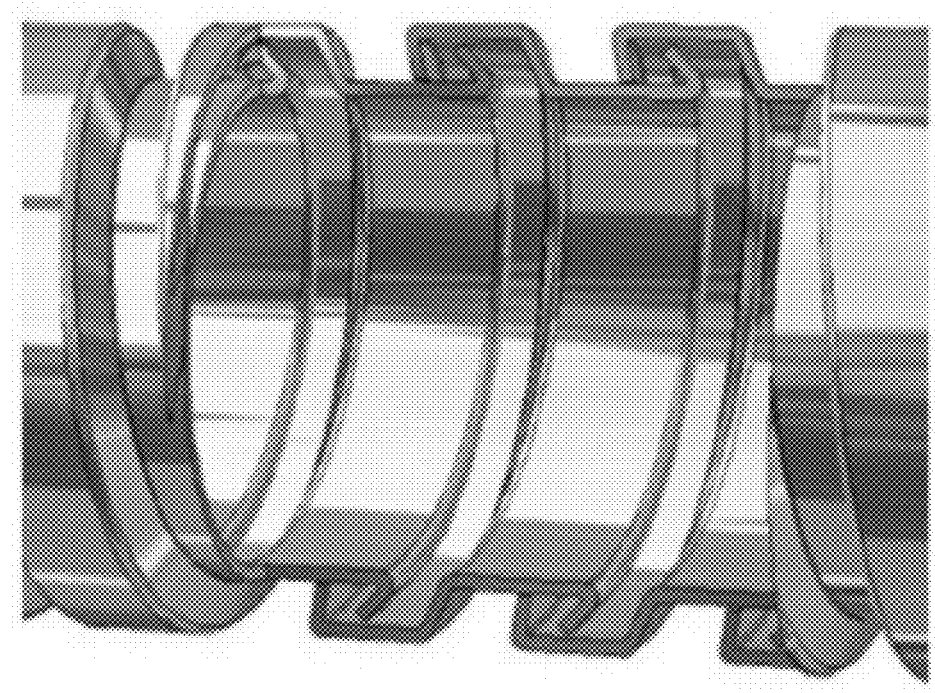
FIG. 31 shows an enlarged view of the catheter apparatus of FIG. 30.
Figure 32:
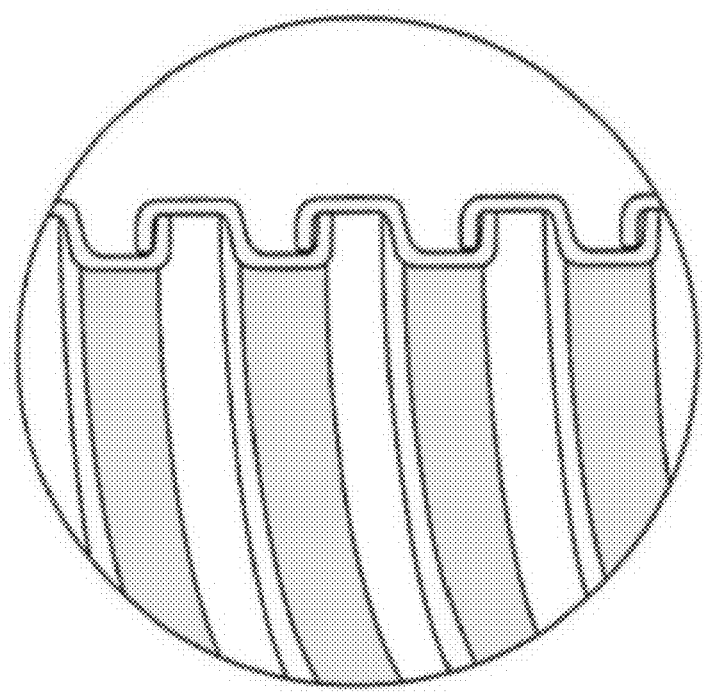
FIG. 32 is an example of a section through the exemplary catheter apparatus of FIG. 30, in a slightly enlarged view.

FIGS. 30-32 illustrate an alternative variation of a bend-limited catheter in which flexible metal conduit is miniaturized and used to form the bend-limited catheter. In this example, flat ribbon is shaped into rings or a helix, and is formed into a long tube, as shown. The formed shapes interact with each other to allow and limit tube bending.

Any of the bend-limited catheters described herein may be configured as bend-limited catheter devices having multiple different patterns of interlocking and alternating teeth extending around the tubular body, formed by the one or more cut-out kerf. The pattern of interlocking and alternating teeth may repeat from a distal region to a proximal region of the length of the tubular body. As already described above, each tooth of the interlocking and alternating teeth may comprise a head region that is wider than a base region, arranged so that the head regions alternate with base regions radially around the tubular body, so that the catheter bends in a direction out of a long axis of the catheter device up to a locking radius, beyond which the tubular body does not allow further bending in the direction. Each tooth of the interlocking and alternating teeth may form a tooth angle between a line extending through a width of the head region (e.g. or along the flattened head region) and a line extending from the head region and the base region (e.g., the sides), as described above.

These devices may include a proximal pattern and a more distal pattern that have different properties, and in particular, have different average tooth angles and/or different ratios of pitch to tubular body diameter. For example, the average tooth angle of the distal region may be greater than the average tooth angle of the more proximal region.

Figure 33A:
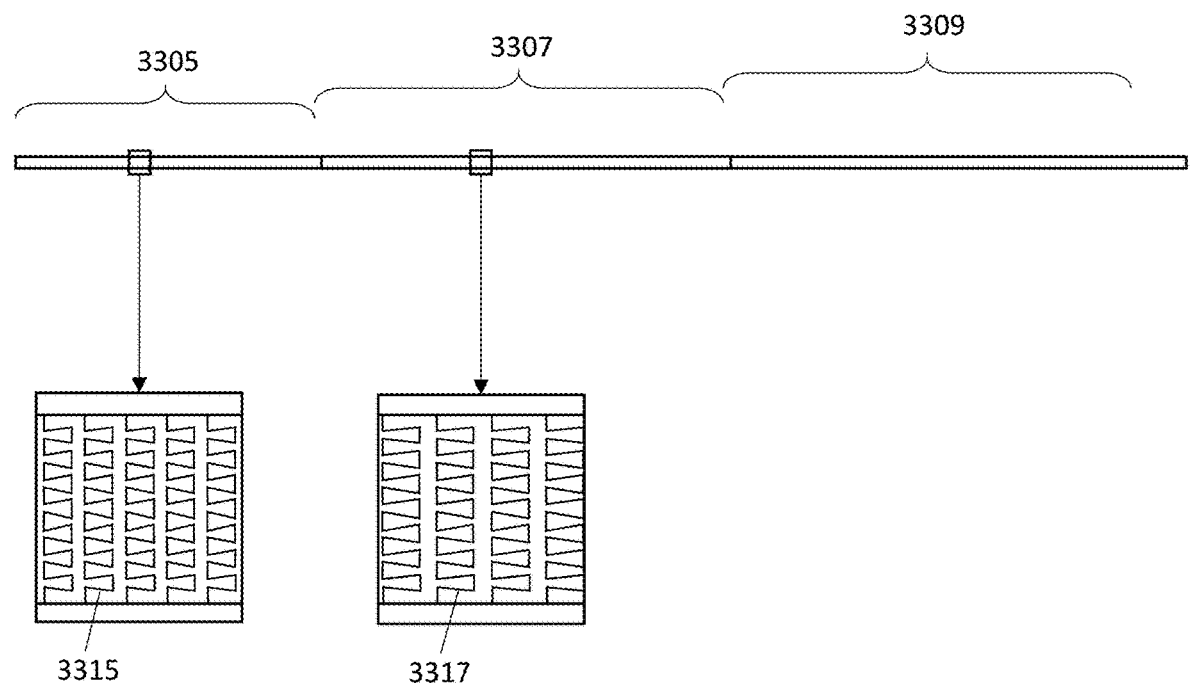
FIG. 33A schematically illustrates an example of a bend-limited catheter device having a plurality of different regions with different bend diameters (and therefore locking bend angles).

FIG. 33A illustrates one example of a bend-limited catheter device having a distal (e.g., first) region 3305 that having different properties than the more proximal 3307 (e.g., second) region. The first region is located immediately adjacent to the second region, though they may be separated by an intervening region. One or more additional regions 3309 may be arranged proximal and/or distal (or between) the first and second regions. In some variations the distal end region 3305 may begin at the distal end of the catheter and may extend for up to 30 or more (e.g., up to about 20, about 22, about 23, about 24, about 25, about 26, about 27, about 28, about 29, about 30, about 31, about 32, about 33, about 35, etc.) cm. The proximal region may be calibrated to be in the aortic region for a neurovascular catheter, and may extend from the distal region for another 20-35 cm (e.g., about 20 cm, about 21 cm, about 22 cm, about 23 cm, about 24 cm, about 25 cm, about 26 cm, about 27 cm, about 28 cm, about 29 cm, about 30 cm, etc.).

In FIG. 33A, the catheter is configured so that the distal region has a higher flexibility and smaller locking angle (e.g., larger locking angle relative to the long axis of the catheter). This may be achieved by using a pattern of interlocking and alternating keystone-shaped teeth extending around the tubular body for the distal portion 3305 in which the pattern of interlocking and alternating keystone-shaped teeth may extends more than 2 cm along the length of the long axis (e.g., between 2 and 30 cm, e.g., between 2-29 cm, between 3-28 cm, between 3-27 cm, between 4-26 cm, between 4-25 cm, between 4-24 cm, between 4-23 cm, etc.) comprises keystone-shaped teeth having a tooth angle that is between 61-84 degrees (e.g., about 78 degrees in one example). This is illustrated in the enlarged region 3315 of FIG. 33A. The more proximal portion 3307 of the pattern of interlocking and alternating keystone-shaped teeth may extend more than 2 cm along the length of the long axis (e.g., may extent between 2 and 30 cm, e.g., between 2-29 cm, between 3-28 cm, between 3-27 cm, between 4-26 cm, between 4-25 cm, between 4-24 cm, between 4-23 cm, etc.) may have keystone-shaped teeth having a tooth angle that is between 30 to 60 degrees (e.g., about 58 degrees in one example). This is illustrated in the enlarged region 3317 of FIG. 33A. The distal portion of the pattern of interlocking and alternating keystone-shaped teeth may have a pitch to tubular body diameter ratio that is between 0.09 and 0.30 and a pitch to tubular body diameter ratio of the more proximal portion of the pattern of interlocking and alternating keystone-shaped teeth is between 0.30 and 0.90.

Figure 33B:
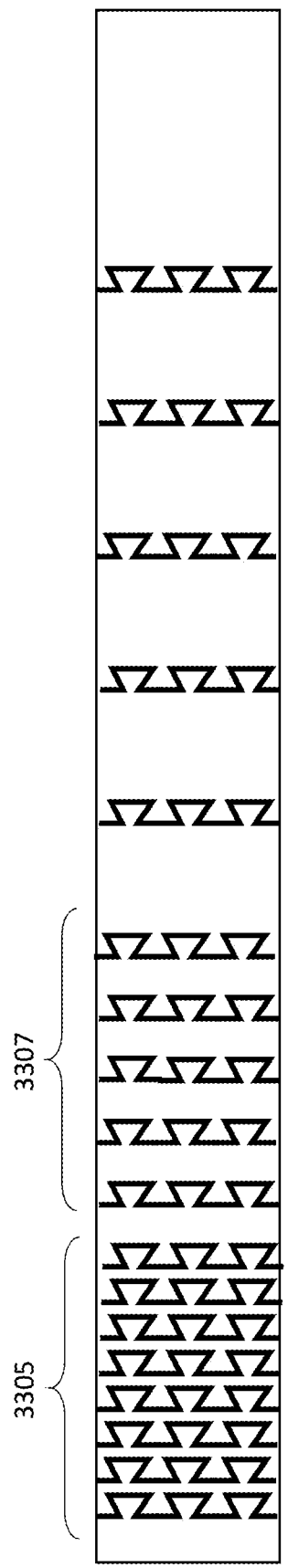
FIG. 33B is a schematic example of a bend-limited catheter device having a non-spiral design or pattern of interlocking keystone teeth radially wrapping around the perimeter of the catheter with a variable (shown as decreasing) density of interlocking keystone teeth along the distal to proximal length of the catheter.
Figure 33C:
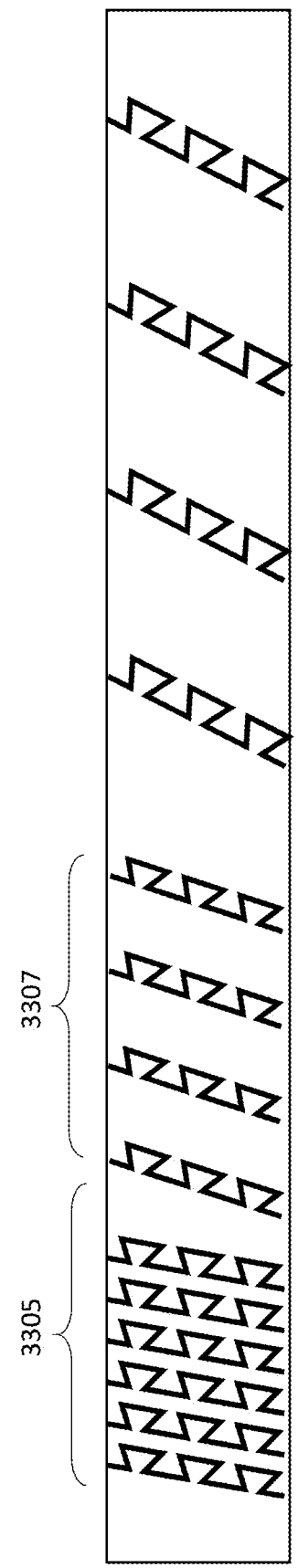
FIG. 33C is a schematic example of a bend-limited catheter device having a spiral, e.g., helical, pattern of interlocking keystone teeth radially wrapping around the perimeter of the catheter with a variable (also shown as decreasing) density of interlocking keystone teeth along the distal to proximal length of the catheter.

FIGS. 33B and 33C illustrate other examples of bend-limited catheters including multiple regions along their length (including distal region and proximal regions) having different locking bend angles, smoothness, and/or flexibility. For example in FIGS. 33A and 33B, the proximal region has a much smaller pitch/tube diameter compared to the more proximal region. FIG. 33A shows an example in which the pattern of interlocking teeth are formed by multiple cut-out kerfs into multiple parallel, transverse rows; FIG. 33B shows a single helically wound cut-out kerf forming multiple rows of interlocking teeth.

Figure 34A:
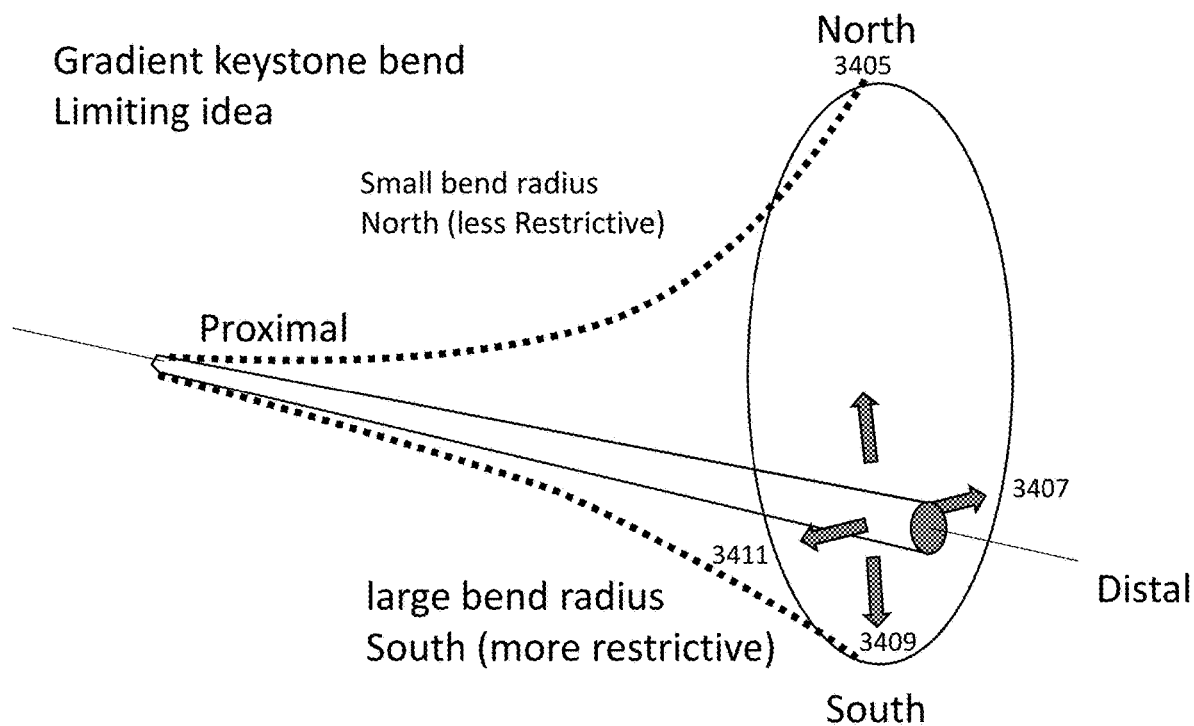
FIG. 34A shows an example of a non-uniformly bend-limited catheter that is configured to have different locking radiuses in different directions out of the long axis of the catheter, beyond which the tubular body does not allow further bending. The catheter may bend freely (e.g., with little if any force required to bend the catheter) until the catheter is bent to a curve having a bend radius that exceeds the locking radius (e.g., then the bend angle is greater than or equal to the locking bend angle)

As mentioned above, any of the devices described herein may be non-uniformly bend-limited catheter devices that may include regions of different locking radiuses around the perimeter of the bend-limited region, as illustrated in FIG. 34A. Such devices may be adjustable by rotating the catheter shaft axially, and may therefore act as an active lock/stabilizer in a vessel. In FIG. 34, the bend-limited catheter includes a much smaller locking bend angle, β (a much larger locking bend angle relative to the long axis of the catheter, α, as shown in FIG. 6) in the "north" direction 3405; the east 3307, west 3311 and south 3309 directions all have similar locking bend angles, as shown, resulting in the non-uniform bending limiting property of the catheter. This may be achieved by adjusting the pattern of interlocking and alternating teeth, as described herein.

Figure 34B:
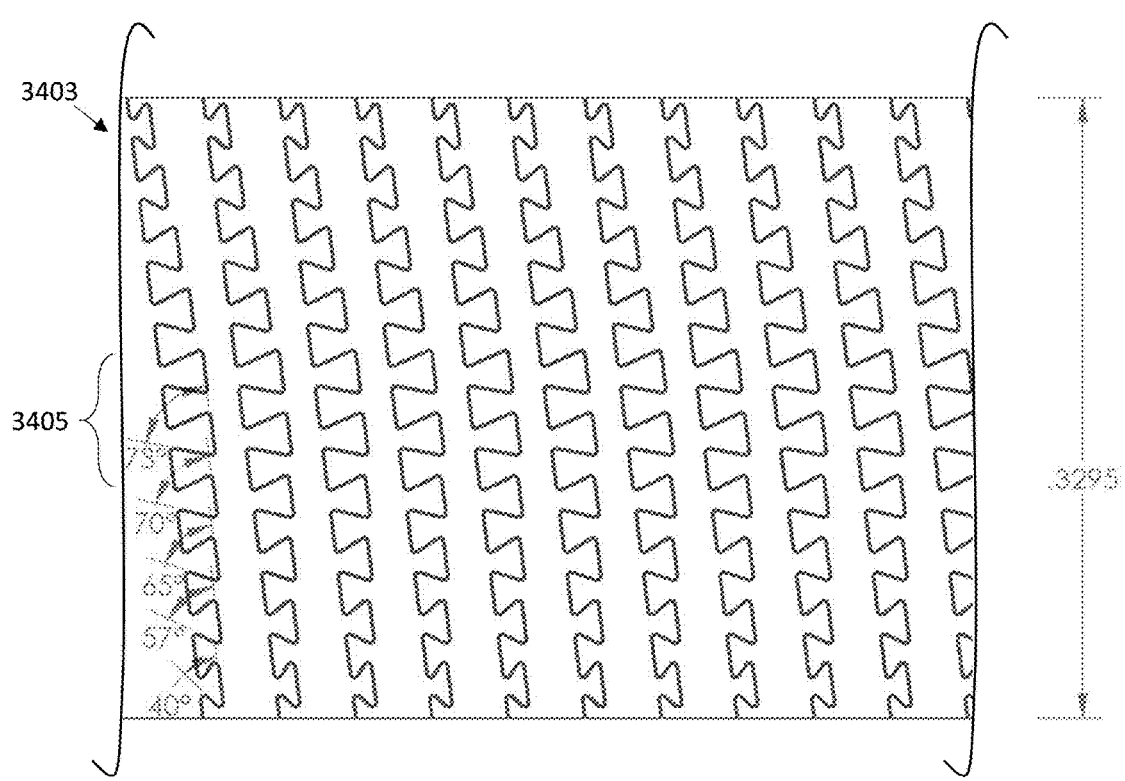
FIG. 34B is an example of a keystone-shaped pattern (showing the top or north side of the catheter) that is non-uniform around the perimeter of the catheter, arranged so that each tooth of the interlocking and alternating teeth shown forms a tooth angle between a line extending through a width of the head region (e.g., the flattened top of the keystone-shaped tooth) and a line extending from the head region and the base region (the angled-in wall(s) of the keystone-shaped tooth), and the tooth angles of the interlocking and alternating teeth vary radially around the tubular body so that the locking radius of the portion of the length of the tubular body varies radially around the tubular body.

The teeth (e.g., keystone-shaped teeth) may form a gradient around the perimeter create a bend limiting element. The keystone gradient may be engineered to produce different amounts of limiting (bend radius bias) depending on the direction the tube is bent. A catheter made with the gradient bias would be able to bend around tight turns (small bend radius) and by torqueing the proximal catheter end from 0 to less than 180 degrees (half a turn) the bend radius limiting element would increase and the catheter would create an adjustable locking zone (more to less bending), to provide an adjustable locking within a vessel (e.g., wedging to wall or tangent touch points), and/or remove the access limiting nature of a fixed single bend limiting keystone. The locking angle (and correspondingly, the locking diameter/locking radius) may be tuned or adjusted in a non-uniform manner around the perimeter of the catheter. FIG. 34B shows an example of a portion of a cut-out kerf pattern for a bend-limited catheter that has a non-uniform locking bend angle around the circumference of the catheter.

In FIG. 34B, for example, the keystone-shaped teeth are arranged in longitudinally parallel sets of teeth having different tooth angles (and in this example, different tooth heights) that provide for differential locking bend angles, and therefore a bias bend configuration (e.g., bending is biased more in one direction, e.g., north, than in other directions). In FIG. 34B, the tooth angles at the top 3403 of the tubular body have a tooth angle (e.g., about 40 degrees), which may be the bend angle for teeth on the back side of the catheter (not shown). The middle region 3405 has a tooth angle of 73 degrees, which decreases for the teeth on either side of the middle row (e.g., to 70 degrees, 65 degrees and 57 degrees, back to 40 degrees). The height of each tooth also decreases as the teeth move away from the line of teeth corresponding to the 'north' (e.g., the middle region 3405) in the pattern. The larger pitch of these middle teeth may allow the contact surfaces of the sides to slide more, providing a larger expansion area in these teeth, and therefore greater bending (e.g., larger locking bend angle relative to the long axis of the catheter, α).

Figure 35A:
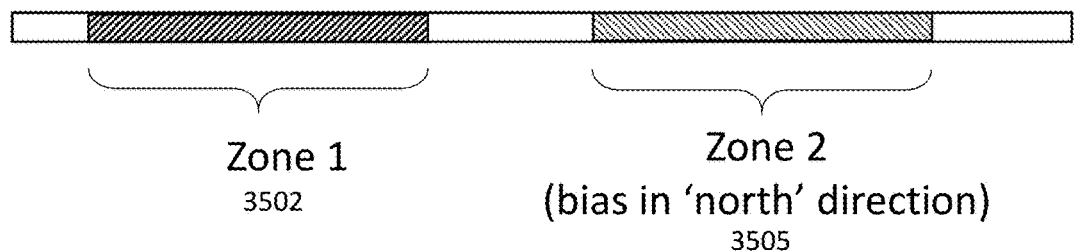
FIG. 35A is an example of a bend-limited catheter device having multiple regions of one or more cut-out kerfs forming a pattern of interlocking and alternating teeth extending around the tubular body; in this example, one of the regions ("zone 2") is configured to have a greater locking radius (and therefore the locking bend angle) in one direction.
Figure 35B:
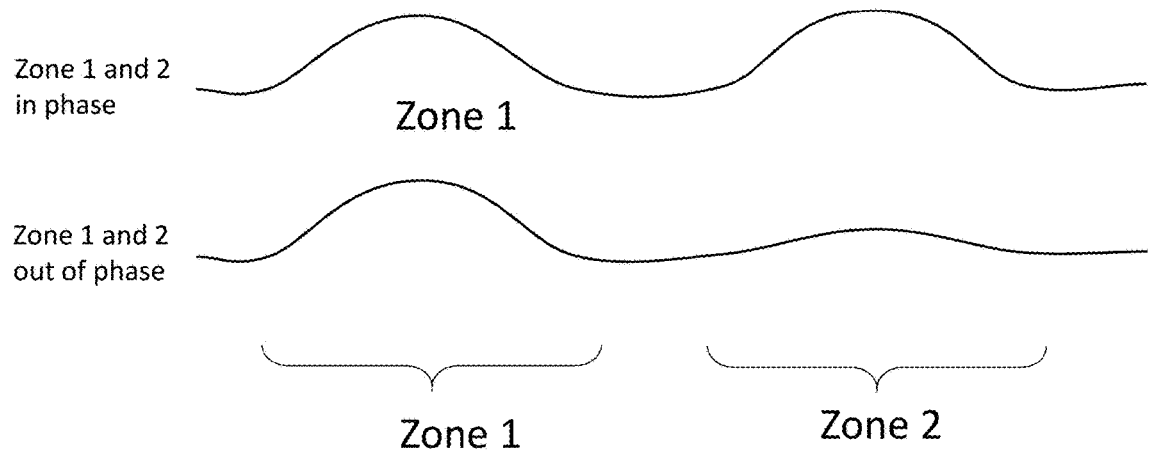
FIG. 35B shows curve profiles of the exemplary bend-limited catheter of FIG. 35A illustrating the different bend locking radiuses for the different regions in different directions or orientations.
Figure 35C:
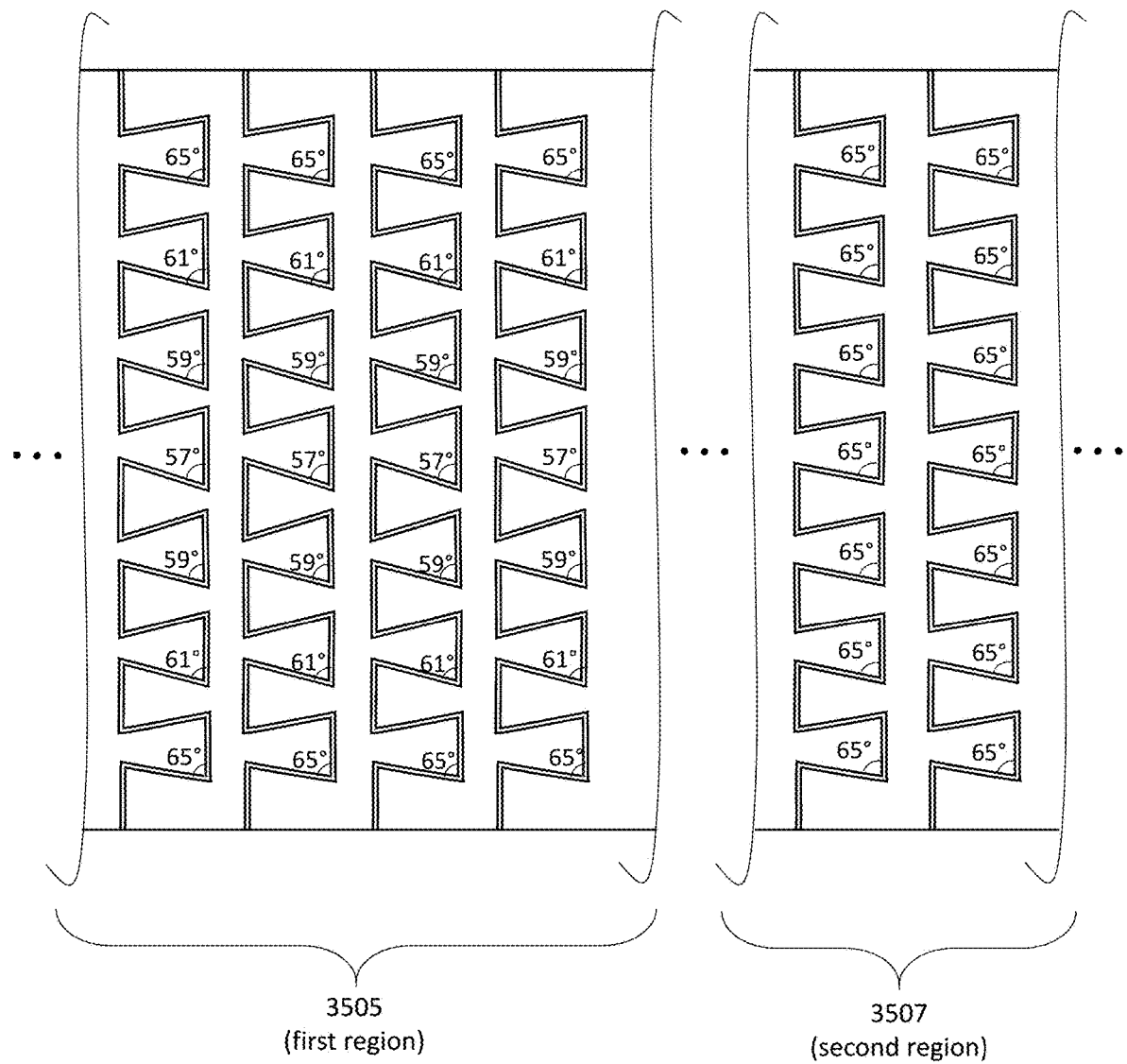
FIG. 35C is an example of portions of a bend-limited catheter device such as that shown in FIG. 35A, showing different regions along the elongate body of the catheter; the first region is configured to have different locking radiuses around the perimeter of the catheter (e.g., by modifying the tooth angles of the keystone-shaped teeth), and the second region is configured to have a uniform locking radius around the perimeter.

The bias bend design can be continuous the whole catheter length, it can is limited zone length, it can be spread between two zones (one more proximal), bend limits in 2 zones can be out of phase to create an S curves like property control. For example, FIGS. 35A-35C illustrate an example of a catheter having multiple regions of bending limiting around their perimeter, in which at least one of these regions has non-uniform bend limiting. FIG. 35A shows a distal bend-limited region ("zone A") 3502 and a proximal bend-limited region ("Zone B") 3505. In this example, the second zone 3505 has a bend-limited bias that is oriented in the north direction (e.g., up, as shown in FIG. 34A, e.g., at 180 degrees if measured radially with south being 0 degrees). The proximal zone may be uniformly bend-limited or may also be non-uniformly bend limiting.

FIG. 34B illustrates an example of a curvature profile for a catheter similar to that shown in FIG. 34A in which the second zone (3505') is biased.

FIG. 35C shows an example of two regions of a catheter including a first region 3505 that is non-uniformly bend-limited and a second region that is uniformly bend-limited. In this example, the first region includes different teeth angles in teeth aligning down the long axis of the catheter, as shown. The second region also include a pattern of interlocking and alternating teeth, but all of these teeth having the same tooth angle around the circumference of the catheter, as shown. In this example the tooth height is approximately the same for all teeth; the tooth heights in the non-uniformly bend-limited region may instead vary, as described above.

Figure 36:
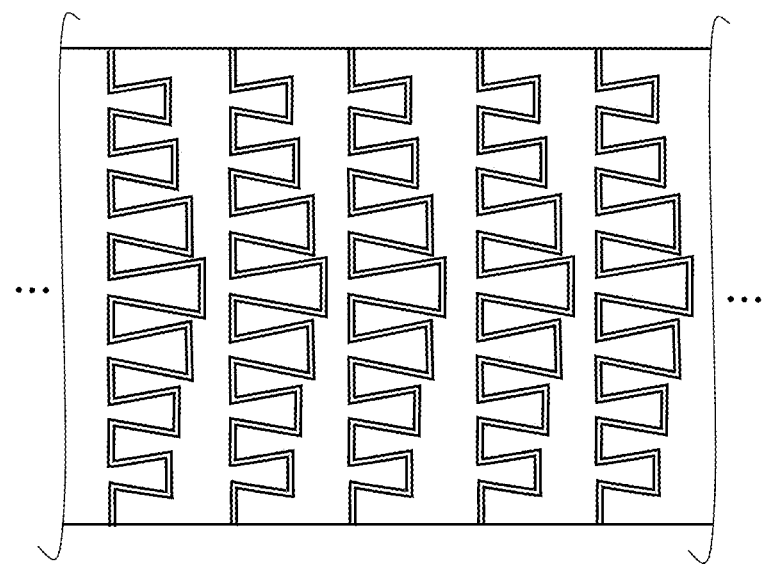
FIG. 36 is an example of a portion of a non-uniformly bend-limited catheter device having different locking radiuses around the perimeter of the catheter (e.g., by modifying the shape and/or size of the keystone-shaped teeth.
Figure 37:
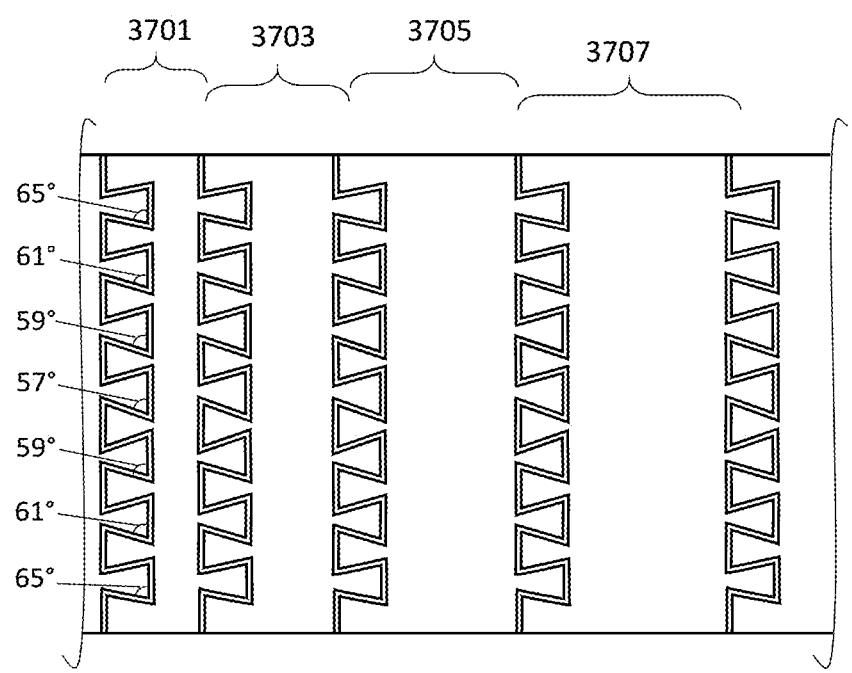
FIG. 37 is an example of a non-uniformly bend-limited catheter device in which the pitch between longitudinally-adjacent teeth changes over the length of the catheter device, similar to that shown in FIGS. 33A-33C.

FIGS. 36 and 37 illustrate alternative embodiments of cut-out kerfs forming a pattern of interlocking and alternating teeth extending around the tubular body. For example, in FIG. 36, the height of the teeth various around the circumference of the tubular body, which may modify the smoothing, strength, flexibility and locking bend angle of the catheter, as described above. In FIG. 37, the pitch 3701, 3703, 3705, 3707 increases along the length (distal to proximal) of the catheter, similar to that shown in FIG. 33C.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A non-uniformly bend-limited catheter device having a length extending in a long axis, the device comprising:
    a tubular body formed of a rigid material having one or more cut-out kerfs forming a pattern of interlocking and alternating teeth extending around the tubular body, wherein each tooth of the interlocking and alternating teeth each comprise a head region that is wider than a base region, arranged so that the head regions alternate with base regions radially around the tubular body, so that the tubular body bends freely out of the long axis up to a locking radius, beyond which the tubular body does not allow further bending;
    wherein each tooth of the interlocking and alternating teeth forms a tooth angle between a line extending through a width of the head region and a line extending from the head region and the base region, further wherein the tooth angles of the interlocking and alternating teeth vary radially around the tubular body so that the locking radius of a portion of the length of the tubular body varies radially around the tubular body; and wherein a second region of the length of the tubular body that comprises a second one or more cut-out kerfs forming a second pattern of interlocking and alternating teeth extending around the tubular body, so that the second region of the tubular body bends freely out of the long axis up to a second locking radius, beyond which the tubular body does not allow further bending.

2. The device of claim 1, wherein the tooth angles vary between 10 degrees and 89 degrees.

3. The device of claim 1, wherein the pattern of interlocking and alternating teeth and the cut-out kerf are configured so that the tubular body expands in the long axis from a compressed length to a maximally expanded length by between about 0.005 inches per every 0.1 inch of the length of the pattern of interlocking and alternating teeth and 0.085 inches per every 0.1 inch of the length of the pattern of interlocking and alternating teeth.

4. The device of claim 1, wherein the distance between the head region and the base region of the teeth varies radially around the tubular body.

5. The device of claim 1, wherein the tubular body comprises a metal or rigid polymeric material.

6. The device of claim 1, wherein the tubular body comprises one or more of: steel, tungsten, and Nitinol.

7. The device of claim 1, wherein the pattern of interlocking and alternating teeth extends helically around the tubular body.

8. The device of claim 1, further comprising a sealing material extending across the cut-out kerf.

9. The device of claim 8, wherein the sealing material is laminated to the rigid tubular body.

10. The device of claim 8, wherein the sealing material is laminated to an inner surface of the rigid tubular body.

11. The device of claim 1, wherein the teeth each form a keystone shape.

12. The device of claim 1, wherein the teeth each form one of: a keystone shape, a mushroom shape, and a T-shape.

13. The device of claim 1, further comprising an inflatable balloon on the catheter.

14. The device of claim 1, wherein the locking radius is between 0.2 cm and 32 cm.

15. The device of claim 1, wherein the locking radius is different from the second locking radius at one more positions radially around the tubular body.

16. The device of claim 1, wherein the tooth angles of the interlocking and alternating teeth vary radially in a continuous gradient around the tubular body so that the locking radius of a portion of the length of the tubular body varies radially and continuously around the tubular body.

17. A non-uniformly bend-limited catheter device having an elongate length extending in a long axis, the device comprising:
    a tubular body formed of a rigid material having a cut-out kerf forming a pattern of interlocking and alternating teeth extending around the tubular body, wherein the interlocking and alternating teeth each comprise a head region that is wider than a base region, arranged so that the head regions alternate with base regions radially around the tubular body;
    wherein the pattern of interlocking and alternating teeth and the cut-out kerf are configured so that the tubular body expands in the long axis from a compressed length to a maximally expanded length by between about 0.005 inches per every 0.1 inch of the length of the pattern of interlocking and alternating teeth and 0.085 inches per every 0.1 inch of the length of the pattern of interlocking and alternating teeth, so that the tubular body bends freely out of the long axis up to a locking radius, beyond which the tubular body does not allow further bending;

further wherein each tooth of the interlocking and alternating teeth forms a tooth angle between a line extending through a width of the head region and a line extending between the head region and the base region, wherein the tooth angles of the interlocking and alternating teeth vary radially around the perimeter of the tubular body, so that the locking radius varies around the perimeter of the tubular body; and a sealing material extending across the cut-out kerf; and wherein a second region of the length of the tubular body that comprises a second one or more cut-out kerfs forming a second pattern of interlocking and alternating teeth extending around the tubular body, so that the second region of the tubular body bends freely out of the long axis up to a second locking radius, beyond which the tubular body does not allow further bending.

18. The device of claim 17, wherein the tooth angles vary between 10 degrees and 89 degrees.

19. The device of claim 17, wherein the distance between the head region and the base region of the teeth varies radially around the tubular body.

20. The device of claim 17, wherein the tubular body comprises one or more of: steel, tungsten, and Nitinol.

21. The device of claim 17, wherein the pattern of interlocking and alternating teeth extends helically around the tubular body.

22. The device of claim 17, wherein the sealing material is laminated to the rigid tubular body.

23. The device of claim 17, wherein the teeth each form one of: a keystone shape, a mushroom shape, and a T-shape.

24. The device of claim 17, further comprising an inflatable balloon on the catheter.

25. The device of claim 17, wherein the locking radius is between 0.2 cm and 32 cm.

26. The device of claim 17, wherein the locking radius is different from the second locking radius at one more positions radially around the tubular body.

27. A non-uniformly bend-limited catheter device having an elongate length extending in a long axis, the device comprising:

a tubular body formed of a rigid material having a cut-out kerf forming a pattern of interlocking and alternating teeth extending around the tubular body, wherein the interlocking and alternating teeth each comprise a keystone shape having a flattened head region that is wider than a base region, arranged so that the flattened head regions alternate with base regions radially around the tubular body;

wherein the pattern of interlocking and alternating teeth and the cut-out kerf are configured so that the tubular body bends freely out of the long axis up to a locking radius, beyond which the tubular body does not allow further bending;

further wherein each tooth of the interlocking and alternating teeth forms a tooth angle between a line extending through a width of the flattened head region and a line extending between the flattened head region and the base region, wherein the tooth angles of the interlocking and alternating teeth vary radially around the perimeter of the tubular body, so that the locking radius varies around the perimeter of the tubular body; and a sealing material extending across the cut-out kerf; and wherein a second region of the length of the tubular body that comprises a second one or more cut-out kerfs forming a second pattern of interlocking and alternating teeth extending around the tubular body, so that the second region of the tubular body bends freely out of the long axis up to a second locking radius, beyond which the tubular body does not allow further bending.

* * * * *